United States Patent [19]

Prendergast et al.

[11] Patent Number: 5,723,581
[45] Date of Patent: Mar. 3, 1998

[54] MURINE AND HUMAN BOX-DEPENDENT MYC-INTERACTING PROTEIN (BIN1)

[75] Inventors: George C. Prendergast, Doylestown; Daitoku Sakamuro, Philadelphia, both of Pa.

[73] Assignee: The Wistar Institute of Anatomy and Biology, Philadelphia, Pa.

[21] Appl. No.: 652,972

[22] Filed: May 24, 1996

Related U.S. Application Data

[63] Continuation-in-part of Ser. No. 435,454, May 5, 1995, Pat. No. 5,605,830.

[51] Int. Cl.$^6$ .................... C07K 14/00; C07K 14/435
[52] U.S. Cl. .................... 530/350; 530/827; 530/828; 514/2; 514/44
[58] Field of Search .................... 514/2, 44; 530/350, 530/827, 828; 536/23.1, 23.5

[56] References Cited

U.S. PATENT DOCUMENTS 4,419,446  12/1983  Howley et al. .................... 435/69.1

FOREIGN PATENT DOCUMENTS

WO91/18088  11/1991  WIPO.

OTHER PUBLICATIONS

M. Cole, "The myc Oncogene: Its Role in Transformation and Differentiation", *Ann. Rev. Genet.*, 20:361–384 (1986).

D. Askew et al, "Constitutive c–myc Expression in an Il–3–dependent Myeloid Cell Line Suppresses Cell Cycle Arrest and Accelerates Apoptosis", *Oncogene*, 6:1915–1922 (Oct., 1991).

G. Evan et al, "Induction of Apoptosis in Fibroblasts by c–myc Protein", *Cell*, 69:119–128 (Apr. 3, 1992).

D. Sheiness et al, "Identification of Nucleotide Sequences which May Encode the Oncogenic Capacity of Avian Retrovirus MC29", *J. Virol.*, 28(2):600–610 (Nov., 1978).

T. Strohmeyer et al, "Review Article—Proto–Oncogenes and Tumor Suppressor Genes in Human Urological Malignancies", *J. Urol.*, 151:1479–1497 (Jun. 1994).

M–J. Gething et al, "Cell–surface Expression of Influenza Haemagglutinin from a Cloned DNA Copy of the RNA Gene", *Nature*, 293:620–625 (Oct. 22, 1981).

R. Kaufman et al, "Coamplification and Coexpression of Human Tissue–Type Plasminogen Activator and Murine Dihydrofolate Reductase Sequences in Chinese Hamster Ovary Cells", *Mol. Cell. Biol.*, 5(7):1750–1759 (Jul., 1985).

M. Kay et al, "In vivo Hepatic Gene Therapy: Complete Albeit Transient Correction of Factor IX Deficiency in Hemophilia B Dogs", *Proc. Natl. Acad. Aci. USA*, 91:2353–2357 (Mar. 1994).

S. Ishibashi et al, "Hypercholesterolemia in Low Density Lipoprotein Receptor Knockout Mice and its Reversal by Adenovirus–mediated Gene Delivery", *J. Clin. Invest.*, 92:883–893 (Aug., 1993).

W. Huse et al, "Research Article—Generation of a Large Combinatorial Library of the Immunoglobuline Repertoire in Phage Lambda", *Science*, 246:1275–1281 (Dec. 8, 1989).

G. Mark et al, "Humanization of Monoclonal Antibodies", Chapter 4, *The Handbook of Experimental Pharmacology*, Springer–Verlag (Jun., 1994).

S. Fields et al, "A Novel Genetic System to Detect Protein–Protein Interactions", *Nature*, 340:245–246 (Jul. 20, 1989).

A. Vojtek et al, "Mammalian Ras Interacts Directly with the Serine/Threonine Kinase Raf", *Cell*, 74:205–214 (Jul. 16, 1993).

G. Prendergast et al, "A New Bind for Myc", *Trends in Genet.*, 8(3):91–97 (Mar., 1992) [Prendergast I].

A. Rustgi et al, "Amino–terminal Domains of c–myc and N–myc Proteins Mediate Binding to the Retinoblastoma Gene Product", *Nature*, 352:541–544 (Aug. 1991).

G. Prendergast et al, "Biphasic Effect of Max on Myc Contransformation Activity and Dependence on Amino– and Carboxy–terminal Max Functions", *Genes Dev.*, 6:2429–2439 (Dec., 1992) [Prendergast II].

A. Kelekar et al, "Immortalization by c–myc, H–ras, and E1a Oncogenes Induces Differential Cellular Gene Expression and Growth Factor Responses", *Mol. Cell. Biol.*, 7(11):3899–3907 (Nov., 1987).

C. Shih et al, "Isolation of a Transforming Sequence from a Human Bladder Carcinoma Cell Line", *Cell*, 29:161–169 (May, 1982).

E. Douglass et al, "A Specific Chromosomal Abnormality in Rhabdosarcoma", *Cytogenet. Cell Genet.*, 45:148–155 (1987).

G. Prendergast et al, "Posttranscriptional Regulation of Cellular Gene Expression by the c–myc Oncogene", *Mol. Cell. Biol.*, 9(1):124–134 (Jan., 1989) [Prendergast III].

F. Bauer et al, "Alteration of a Yeast SH3 Protein Leads to Conditional Viability with Defects in Cytoskeletal and Budding Patterns", *Mol. Cell., Biol.*, 13(8):5070–5084 (Aug., 1993).

B. Lichte et al, "Amphiphysin, a Novel Protein Associated with Synaptic Vesicles", *BMBO J.*, 11(7):2521–2530 (1992).

C. David et al, "Autoimmunity in Stiff–Man Syndrome with Breast Cancer is Targeted to the C–terminal Region of Human Amphiphysin, a Protein Similar to the Yeast Proteins, Rvs167 and Rvs161", *FEBS Letters*, 351:73–79 (Jul., 1994).

(List continued on next page.)

*Primary Examiner*—George C. Elliott
*Assistant Examiner*—Sean McGarry
*Attorney, Agent, or Firm*—Howson and Howson

[57] ABSTRACT

A partial murine cDNA clone, a human cDNA clone, and a partial human genomic clone, each encoding a Box-dependent myc–interacting polypeptide termed Bin1, are provided. Also provided are methods of using the nucleic acid sequences, polypeptides, and antibodies directed against same in the diagnosis and treatment of cancers and hyperplastic disease states.

3 Claims, 6 Drawing Sheets

OTHER PUBLICATIONS

D. Miller et al, "An Insect Baculovirus Host–Vector System for High–Level Expression of Foreign Genes", *Genetic Engineering*, 8:277–298 (1986).

D. Negorev et al, "The Bin1 Gene Localizes to Human Chromosome 2q14 by PCR Analysis of Somatic Cell Hybrids and Fluorescence in Situ Hybridization", *Genomics*, 33:329–331 (Apr., 1996).

Databases EMBL/Genebank/DDBJ on MPSRCH, Accession No. Z24792, Auffray et al, (Jul. 20, 1993) [Auffray I].

Database Genexpress on MPSRCH, Accession No. Z28487, Auffray et al, (Dec., 1993) [Auffray II].

Databases EMBL/GeneBank/DDBJ on MPSRCH, Accession No. F00405, Auffray et al, (Mar. 7, 1995) [Auffray III].

Database Image Consortium, LLNL on MPSRCH, Accession No. R34418, Hillier et al, (May 2, 1995) [Hillier I].

Databases EMBL/GeneBank/DDBJ on MPSRCH, Accession No. Z24784, Auffray et al, (Jul., 30, 1993) [Auffray IV].

The Washington–Merck EST Project on MPSRCH, Accession No. R18250, Hillier et al, (Apr. 14, 1995) [Hillier II].

FIGURE 1

Partial Mouse BIN1 cDNA and Polypeptide
SEQ ID NOS. 1 and 2

| | | | | | | | | | | | | | | |
|---|---|---|---|---|---|---|---|---|---|---|---|---|---|---|
| GAG | ATC | AGA | GTG | AAC | CAT | GAG | CCA | GAG | CCG | GCC | AGT | GGG | GCC | TCA | 45 |
| Glu | Ile | Arg | Val | Asn | His | Glu | Pro | Glu | Pro | Ala | Ser | Gly | Ala | Ser | |
| 1 | | | | 5 | | | | | 10 | | | | | 15 | |

| | | | | | | | | | | | | | | | |
|---|---|---|---|---|---|---|---|---|---|---|---|---|---|---|---|
| CCC | GGG | GCT | GCC | ATC | CCC | AAG | TCC | CCA | TCT | CAG | CCA | GCA | GAG | GCC | 90 |
| Pro | Gly | Ala | Ala | Ile | Pro | Lys | Ser | Pro | Ser | Gln | Pro | Ala | Glu | Ala | |
| | | | | 20 | | | | | 25 | | | | | 30 | |

| | | | | | | | | | | | | | | | |
|---|---|---|---|---|---|---|---|---|---|---|---|---|---|---|---|
| TCC | GAG | GTG | GTG | GGT | GGA | GCC | CAG | GAG | CCA | GGG | GAG | ACA | GCA | GCC | 135 |
| Ser | Glu | Val | Val | Gly | Gly | Ala | Gln | Glu | Pro | Gly | Glu | Thr | Ala | Ala | |
| | | | | 35 | | | | | 40 | | | | | 45 | |

| | | | | | | | | | | | | | | | |
|---|---|---|---|---|---|---|---|---|---|---|---|---|---|---|---|
| AGT | GAA | GCA | ACC | TCC | AGC | TCT | CTT | CCG | GCT | GTG | GTG | GTG | GAG | ACC | 180 |
| Ser | Glu | Ala | Thr | Ser | Ser | Ser | Leu | Pro | Ala | Val | Val | Val | Glu | Thr | |
| | | | | 50 | | | | | 55 | | | | | 60 | |

| | | | | | | | | | | | | | | | |
|---|---|---|---|---|---|---|---|---|---|---|---|---|---|---|---|
| TTC | TCC | GCA | ACT | GTG | AAT | GGG | GCG | GTG | GAG | GGC | AGC | GCT | GGG | ACT | 225 |
| Phe | Ser | Ala | Thr | Val | Asn | Gly | Ala | Val | Glu | Gly | Ser | Ala | Gly | Thr | |
| | | | | 65 | | | | | 70 | | | | | 75 | |

| | | | | | | | | | | | | | | | |
|---|---|---|---|---|---|---|---|---|---|---|---|---|---|---|---|
| GGA | CGC | TTG | GAC | CTG | CCC | CCG | GGA | TTC | ATG | TTC | AAG | GTT | CAA | GCC | 270 |
| Gly | Arg | Leu | Asp | Leu | Pro | Pro | Gly | Phe | Met | Phe | Lys | Val | Gln | Ala | |
| | | | | 80 | | | | | 85 | | | | | 90 | |

| | | | | | | | | | | | | | | | |
|---|---|---|---|---|---|---|---|---|---|---|---|---|---|---|---|
| CAG | CAT | GAT | TAC | ACG | GCC | ACT | GAC | ACT | GAT | GAG | CTG | CAA | CTC | AAA | 315 |
| Gln | His | Asp | Tyr | Thr | Ala | Thr | Asp | Thr | Asp | Glu | Leu | Gln | Leu | Lys | |
| | | | | 95 | | | | | 100 | | | | | 105 | |

| | | | | | | | | | | | | | | | |
|---|---|---|---|---|---|---|---|---|---|---|---|---|---|---|---|
| GCT | GGC | GAT | GTG | GTG | TTG | GTG | ATT | CCT | TTC | CAG | AAC | CCA | GAG | GAG | 360 |
| Ala | Gly | Asp | Val | Val | Leu | Val | Ile | Pro | Phe | Gln | Asn | Pro | Glu | Glu | |
| | | | | 110 | | | | | 115 | | | | | 120 | |

| | | | | | | | | | | | | | |
|---|---|---|---|---|---|---|---|---|---|---|---|---|---|
| CAG | GAT | GAA | GGC | TGG | CTC | ATG | GGT | GTG | AAG | GAG | AGC | GAC | TGA | 402 |
| Gln | Asp | Glu | Gly | Trp | Leu | Met | Gly | Val | Lys | Glu | Ser | Asp | | |
| | | | | 125 | | | | | 130 | | | | | |

FIGURE 2A

Human BIN1 cDNA and Polypeptide
SEQ ID NOS. 3 and 4

```
GAATTCCGTG CTGGTTGAGC TTGCTCATCT CCTTGTGGAA GTTTTCCTCC            50

AGGCCCGCG ATG CTC TGG AAC GTG GTG ACG GCG GGA AAG ATC GCC         95
           Met Leu Trp Asn Val Val Thr Ala Gly Lys Ile Ala
            1               5                       10

AGC AAC GTG CAG AAG AAG CTC ACC CGC GCG CAG GAG AAG GTT CTC      140
Ser Asn Val Gln Lys Lys Leu Thr Arg Ala Gln Glu Lys Val Leu
            15                  20                  25

CAG AAG CTG GGG AAG GCA GAT GAG ACC AAG GAT GAG CAG TTT GAG      185
Gln Lys Leu Gly Lys Ala Asp Glu Thr Lys Asp Glu Gln Phe Glu
            30                  35                  40

CAG TGC GTC CAG AAT TTC AAC AAG CAG CTG ACG GAG GGC ACC CGG      230
Gln Cys Val Gln Asn Phe Asn Lys Gln Leu Thr Glu Gly Thr Arg
            45                  50                  55

CTG CAG AAG GAT CTC CGG ACC TAC CTG GCC TCC GTC AAA GCC ATG      275
Leu Gln Lys Asp Leu Arg Thr Tyr Leu Ala Ser Val Lys Ala Met
            60                  65                  70

CAC GAG GCT TCC AAG AAG CTG AAT GAG TGT CTG CAG GAG GTG TAT      320
His Glu Ala Ser Lys Lys Leu Asn Glu Cys Leu Gln Glu Val Tyr
            75                  80                  85

GAG CCC GAT TGG CCC GGC AGG GAT GAG GCA AAC AAG ATC GCA GAG      365
Glu Pro Asp Trp Pro Gly Arg Asp Glu Ala Asn Lys Ile Ala Glu
            90                  95                  100

AAC AAC GAC CTG CTG TGG ATG GAT TAC CAC CAG AAG CTG GTG GAC      410
Asn Asn Asp Leu Leu Trp Met Asp Tyr His Gln Lys Leu Val Asp
            105                 110                 115

CAG GCG CTG CTG ACC ATG GAC ACG TAC CTG GGC CAG TTC CCC GAC      455
Gln Ala Leu Leu Thr Met Asp Thr Tyr Leu Gly Gln Phe Pro Asp
            120                 125                 130

ATC AAG TCA CGC ATT GCC AAG CGG GGG CGC AAG CTG GTG GAC TAC      500
Ile Lys Ser Arg Ile Ala Lys Arg Gly Arg Lys Leu Val Asp Tyr
            135                 140                 145

GAC AGT GCC CGG CAC CAC TAC GAG TCC CTT CAA ACT GCC AAA AAG      545
Asp Ser Ala Arg His His Tyr Glu Ser Leu Gln Thr Ala Lys Lys
            150                 155                 160
```

FIGURE 2B

```
AAG GAT GAA GCC AAA ATT GCC AAG GCC GAG GAG GAG CTC ATC AAA    590
Lys Asp Glu Ala Lys Ile Ala Lys Ala Glu Glu Glu Leu Ile Lys
        165             170             175

GCC CAG AAG GTG TTT GAG GAG ATG AAT GTG GAT CTG CAG GAG GAG    635
Ala Gln Lys Val Phe Glu Glu Met Asn Val Asp Leu Gln Glu Glu
        180             185             190

CTG CCG TCC CTG TGG AAC AGC CGC GTA GGT TTC TAC GTC AAC ACG    680
Leu Pro Ser Leu Trp Asn Ser Arg Val Gly Phe Tyr Val Asn Thr
        195             200             205

TTC CAG AGC ATC GCG GGC CTG GAG GAA AAC TTC CAC AAG GAG ATG    725
Phe Gln Ser Ile Ala Gly Leu Glu Glu Asn Phe His Lys Glu Met
        210             215             220

AGC AAG CTC AAC CAG AAC CTC AAT GAT GTG CTG GTC GGC CTG GAG    770
Ser Lys Leu Asn Gln Asn Leu Asn Asp Val Leu Val Gly Leu Glu
        225             230             235

AAG CAA CAC GGG AGC AAC ACC TTC ACG GTC AAG GCC CAG CCC AGA    815
Lys Gln His Gly Ser Asn Thr Phe Thr Val Lys Ala Gln Pro Arg
        240             245             250

AAG AAA AGT AAA CTG TTT TCG CGG CTG CGC AGA AAG AAG AAC AGT    860
Lys Lys Ser Lys Leu Phe Ser Arg Leu Arg Arg Lys Lys Asn Ser
        255             260             265

GAC AAC GCG CCT GCA AAA GGG AAC AAG AGC CCT TCG CCT CCA GAT    905
Asp Asn Ala Pro Ala Lys Gly Asn Lys Ser Pro Ser Pro Pro Asp
        270             275             280

GGC TCC CCT GCC GCC ACC CCC GAG ATC AGA GTC AAC CAC GAG CCA    950
Gly Ser Pro Ala Ala Thr Pro Glu Ile Arg Val Asn His Glu Pro
        285             290             295

GAG CCG GCC GGC GGG GCC ACG CCC GGG GCC ACC CTC CCC AAG TCC    995
Glu Pro Ala Gly Gly Ala Thr Pro Gly Ala Thr Leu Pro Lys Ser
        300             305             310

CCA TCT CAG CCA GCA GAG GCC TCG GAG GTG GCG GGT GGG ACC CAA   1040
Pro Ser Gln Pro Ala Glu Ala Ser Glu Val Ala Gly Gly Thr Gln
        315             320             325

CCT GCG GCT GGA GCC CAG GAG CCA GGG GAG ACG GCG GCA AGT GAA   1085
Pro Ala Ala Gly Ala Gln Glu Pro Gly Glu Thr Ala Ala Ser Glu
        330             335             340

GCA GCC TCC AGC TCT CTT CCT GCT GTC GTG GTG GAG ACC TTC CCA   1130
Ala Ala Ser Ser Ser Leu Pro Ala Val Val Val Glu Thr Phe Pro
        345             350             355
```

FIGURE 2C

```
GCA ACT GTG AAT GGC ACC GTG GAG GGC GGC AGT GGG GCC GGG CGC    1175
Ala Thr Val Asn Gly Thr Val Glu Gly Gly Ser Gly Ala Gly Arg
        360             365             370

TTG GAC CTG CCC CCA GGT TTC ATG TTC AAG GTA CAG GCC CAG CAC    1220
Leu Asp Leu Pro Pro Gly Phe Met Phe Lys Val Gln Ala Gln His
        375             380             385

GAC TAC ACG GCC ACT GAC ACA GAC GAG CTG CAG CTC AAG GCT GGT    1265
Asp Tyr Thr Ala Thr Asp Thr Asp Glu Leu Gln Leu Lys Ala Gly
        390             395             400

GAT GTG GTG CTG GTG ATC CCC TTC CAG AAC CCT GAA GAG CAG GAT    1310
Asp Val Val Leu Val Ile Pro Phe Gln Asn Pro Glu Glu Gln Asp
        405             410             415

GAA GGC TGG CTC ATG GGC GTG AAG GAG AGC GAC TGG AAC CAG CAC    1355
Glu Gly Trp Leu Met Gly Val Lys Glu Ser Asp Trp Asn Gln His
        420             425             430

AAG AAG CTG GAG AAG TGC CGT GGC GTC TTC CCC GAG AAC TTC ACT    1400
Lys Lys Leu Glu Lys Cys Arg Gly Val Phe Pro Glu Asn Phe Thr
        435             440             445

GAG AGG GTC CCA TGACGGCGGG GCCCAGGCAG CCTCCGGGCG TGTGAAGAAC    1452
Glu Arg Val Pro
        450

ACCTCCTCCC GAAAAATGTG TGGTTCTTTT TTTTGTTTTG TTTTCGTTTT         1502

TCATCTTTTG AAGAGCAAAG GGAAATCAAG AGGAGACCCC CAGGCAGAGG         1552

GGCGTTCTCC CAAAGTTTAG GTCGTTTTCC AAAGAGCCGC GTCCCGGCAA         1602

GTCCGGCGGA ATTCACCAGT GTTCCTGAAG CTGCTGTGTC CTCTAGTTGA         1652

GTTTCTGGCG CCCCTGCCTG TGCCCGCATG TGTGCCTGGC CGCAGGGCGG         1702

GGCTGGGGGC TGCCGAGCCA CCATACTTAA CTGAAGCTTC GGCCGCACCA         1752

CCCGGGGAAG GGTCCTCTTT TCCTGGCAGC TGCTGTGGGT GGGGCCCAGA         1802

CACCAGCCTA GCCTGCTCTG CCCCGCAGAC GGTCTGTGTG CTGTTTGAAA         1852

ATAAATCTTA GTGTTCAAAA CAAAATGAAA CAAAAAAAAA AATGATAAAA         1902

ACTCTCAAAA AAACAAGGAA TTC                                     1925
```

MURINE AND HUMAN BOX-DEPENDENT MYC-INTERACTING PROTEIN (BIN1)

CROSS-REFERENCE TO RELATED APPLICATION

This is a continuation-in-part of U.S. patent application Ser. No. 08/435,454, filed May 5, 1995, now U.S. Pat. No. 5,605,830.

This invention was made with financial assistance from the National Institutes of Health Grant No. 5-P30-CA-10815-28. The United States government has certain rights in this invention.

FIELD OF THE INVENTION

This invention relates generally to cancer diagnosis and therapy, and more specifically, to cancers associated with the Myc oncoprotein.

BACKGROUND OF THE INVENTION

Myc is a transcription factor and key cell growth regulator that is frequently deregulated in human malignancy, notably Burkitt's and T cell lymphomas, where myc genes suffer chromosomal translocation. In colon and lung carcinomas, myc genes are amplified [M. D. Cole, Ann. Rev. Genet., 20:361–384 (1986)]. Paradoxically, under certain conditions myc can induce apoptosis, a regulated cell suicide process [D. S. Askew et al, Oncogene, 6:1915–1922 (1991); G. I. Evan et al, Cell, 69:119–128 (1992)]. However, loss or suppression of apoptosis is an important step in the malignant conversion of human tumors containing deregulated myc oncogenes, including, prominently, prostate carcinoma [T. G. Strohmeyer et al, J. Urol., 151:1479–1497 (1994)].

There remains a need in the art for compositions and methods of regulating a deregulated Myc protein and of exploiting and/or diagnosing its apoptotic potential.

SUMMARY OF THE INVENTION

In one aspect, the present invention provides a partial murine cDNA clone of a Box-dependent myc-interacting polypeptide 1 (Bin1), formerly referred to as c-Myc interacting peptide (MIP or MIP-99), SEQ ID NO:1, and the polypeptide encoded thereby, SEQ ID NO:2.

In another aspect, the present invention provides a human Bin1 cDNA clone, SEQ ID NO:3, and the human polypeptide encoded thereby, SEQ ID NO:4.

In yet another aspect, the present invention provides a vector comprising a mammalian nucleic acid sequence encoding a Bin1 protein and a host cell transformed by such a vector. Alternatively, this vector may be used in gene therapy applications.

In still another aspect, the invention provides an oligonucleotide probe comprising a nucleic acid sequence as defined herein. Also provided is an antibody raised against a Bin1 protein or peptide thereof.

In yet a further aspect, the present invention provides a diagnostic reagent for breast or liver cancer, or deficient Bin1 production, comprising an oligonucleotide probe or an antibody of the invention.

Further provided is a therapeutic reagent comprising a polypeptide, anti-idiotype antibody, or gene therapy vector of the invention.

Still another aspect of the invention provides a method of treating breast or liver cancer by administering a therapeutic reagent of the invention.

Other aspects and advantages of the present invention are described further in the following detailed description of the preferred embodiments thereof.

BRIEF DESCRIPTION OF THE DRAWINGS

FIG. 1 is a partial murine cDNA sequence SEQ ID NO:1 and the murine Bin1 polypeptide encoded thereby SEQ ID NO:2.

FIG. 2A–2C is a human cDNA sequence SEQ ID NO:3 and the human Bin1 polypeptide encoded thereby SEQ ID NO:4.

DETAILED DESCRIPTION OF THE INVENTION

Figure 3A:
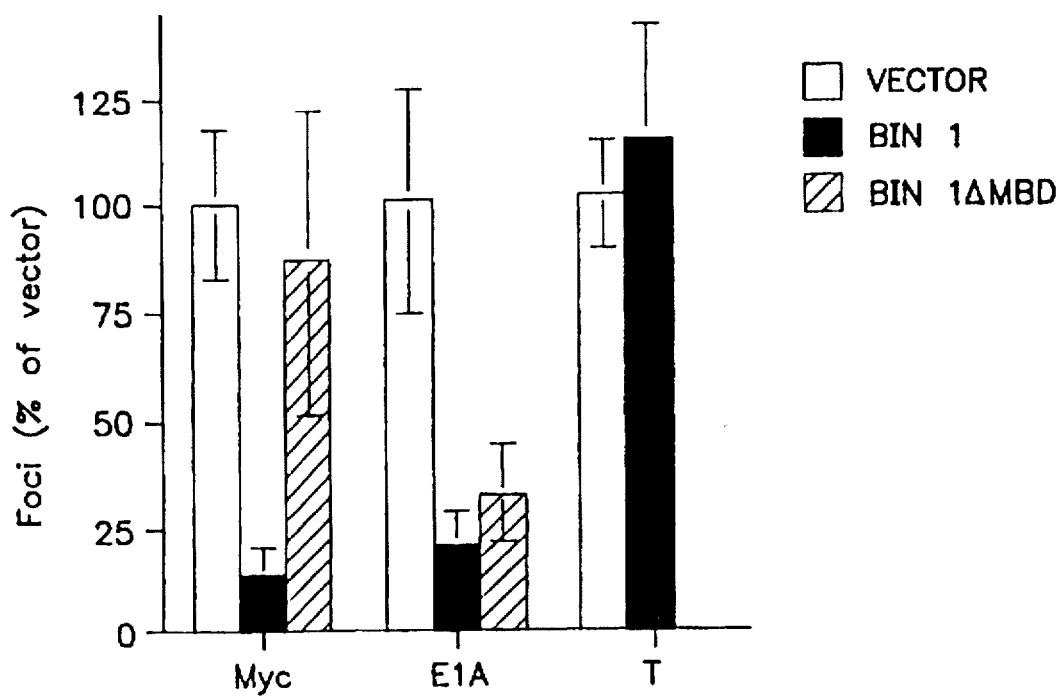
FIG. 3A is a bar chart illustrating the selective requirement of the Myc-binding domain (MBD) for Myc inhibition, as described in Example 7. The data represent three to seven trials for each transfection. The data are depicted as the percent of foci induced by oncogenes and vector, as appropriate.

The present invention provides novel, isolated, nucleic acid sequences which encode novel proteins which interact with c-Myc and bind thereto, fragments of these sequences and antibodies developed thereto. The nucleic acid sequences, protein sequences and antibodies are useful in the detection, diagnosis and treatment of cancers or other disorders associated with deregulation, deficiency or amplification of the c-myc oncogenes. Further, when a Box-dependent myc-interacting polypeptide 1 (called Bin1) of this invention binds to c-Myc, the binding appears to regulate the c-Myc and result in tumor suppression, by inhibiting cell growth and/or facilitating apoptosis (programmed cell death). The Bin1 gene has several other features suggesting it is a tumor suppressor gene. First, Bin1 inhibits Myc-dependent malignant cell transformation. Second, Bin1 is structurally related to RVS167, a negative regulator of the cell division cycle in the yeast Saccharomyces cerevisiae [F. Bauer et al, Mol. Cell. Biol., 13:5070–5084 (1993)]. Third, Northern analysis indicates that expression of Bin1 RNA is ubiquitous in normal tissues but frequently missing in carcinoma cell lines. Fourth, Bin1 selectively inhibits the growth of carcinoma cells lacking endogenous expression. These results show that the observed expression deficits are functionally significant, rather than simply correlated with loss of genomic integrity, and formally demonstrate that Bin1 can act as a tumor suppressor. Fifth, chromosomal mapping has identified Bin1's location at 2q14, a locus lying within a mid-2q region deleted in 50% of metastatic prostate cancers [W. Isaacs, Johns Hopkins Medical School, personal communication] and, at the syntenic murine locus, in 90% of radiation-induced leukemias [I. Hayata et al, Cancer Res., 43:367–373 (1983)]. Thus, Bin1 has been identified as a tumor suppressor gene, similar to the breast cancer gene BRCA1, and the genes encoding p53 and the Rb retinoblastoma protein, which are negative regulators of cell growth that are observed to be mutated and/or unexpressed in human cancer cells. The Bin1 protein specifically interacts with Myc and inhibits its oncogenic activity. These aspects of the invention are discussed in more detail below.

I. Nucleic Acid Sequences

The present invention provides mammalian nucleic acid sequences encoding a Box-dependent myc-interacting polypeptide 1, termed herein Bin1. The nucleic acid sequences of this invention are isolated from cellular materials with which they are naturally associated. In one embodiment, a Bin1 nucleic acid sequence is selected from all or part of the partial murine cDNA clone, SEQ ID NO: 1. In another embodiment, a Bin1 nucleic acid sequence is selected from all or part of a human cDNA clone, SEQ ID NO: 3. In yet another embodiment, the present invention provides a partial Bin1 genomic sequence, SEQ ID NO: 6. However, the present invention is not limited to these nucleic acid sequences.

Given the sequences of SEQ ID NO: 1, SEQ ID NO: 3, and SEQ ID NO: 6, one of skill in the art can readily obtain the corresponding anti-sense strands of these cDNA and genomic sequences. Further, using known techniques, one of skill in the art can readily obtain further genomic sequences corresponding to these cDNA sequences or the corresponding RNA sequences, as desired.

Similarly the availability of SEQ ID NOS: 1, 3 and 6 of this invention permits one of skill in the art to obtain other species Bin1 analogs, by use of the nucleic acid sequences of this invention as probes in a conventional technique, e.g., polymerase chain reaction. Allelic variants of these sequences within a species (i.e., nucleotide sequences containing some individual nucleotide differences from a more commonly occurring sequence within a species, but which nevertheless encode the same protein) such as other human variants of Bin1 SEQ ID NO: 3, may also be readily obtained given the knowledge of this sequence provided by this invention.

The present invention further encompasses nucleic acid sequences capable of hybridizing under stringent conditions [see, J. Sambrook et al, *Molecular Cloning: A Laboratory Manual*, 2d ed., Cold Spring Harbor Laboratory (1989)] to the sequences of SEQ ID NO: 1, SEQ ID NO: 3, SEQ ID NO: 6, their anti-sense strands, or biologically active fragments thereof. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g. hybridization in 4×SSC at 55° C., followed by washing in 0.1×SSC at 37° C. for an hour. An alternative exemplary moderately high stringency hybridization condition is in 50% formamide, 4×SSC at 30° C.

Also encompassed within this invention are fragments of the above-identified nucleic acid sequences. Preferably, such fragments are characterized by encoding a biologically active portion of Bin1, e.g., an epitope. Generally, these oligonucleotide fragments are at least 15 nucleotides in length. However, oligonucleotide fragments of varying sizes may be selected as desired. Such fragments may be used for such purposes as performing the PCR, e.g., on a biopsied tissue sample. For example, one fragment which is anticipated to be particularly useful is the Src homology 3 (SH3) domain, which is located at about nucleotides 1191–1412 of SEQ ID NO: 3 (which encode amino acid residues 378–451 of SEQ ID NO: 4). Preliminary data has indicated this domain may be useful in blocking apoptosis. Other useful fragments include about nucleotides 813–854 of SEQ ID NO: 3 (encoding a nuclear localization signal, amino acid residues about 252–265 of SEQ ID NO: 4), nucleotides about 867–1206 (a Myc-binding domain or MBD amino acids 270–383). Other useful fragments may be readily identified by one of skill in the art by resort to conventional techniques.

The nucleotide sequences of the invention may be isolated by conventional uses of polymerase chain reaction or cloning techniques such as those described in obtaining the murine and human sequences, described below. Alternatively, these sequences may be constructed using conventional genetic engineering or chemical synthesis techniques.

According to the invention, the nucleic acid sequences [SEQ ID NO: 1, SEQ ID NO: 3, and SEQ ID NO: 6] may be modified. Utilizing the sequence data in these figures and in the sequence listing, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are mutants of the Bin1 gene provided herein. Such mutants include amino terminal, carboxy terminal or internal deletions which are useful as dominant inhibitor genes. Such a truncated, or deletion, mutant may be expressed for the purpose of inhibiting the activity of the full-length or wild-type gene. For example, it has been found that expression of the partial murine Bin1 provided herein [SEQ ID NO:2] acts in a dominant inhibitory manner to suppress normal Bin1 activity. Expression of this protein is described in Example 4 below. Another mutant encodes Bin1 deleted in the region encoding the MBD domain (amino acid residues 270–383 of SEQ ID NO: 4).

The invention further provides the complete human Bin1 gene, which has been cloned as a 35–45 kb contiguous sequence from a lambda phage genomic library. The DNA sequence of approximately 15 kb (from the 3' end) of the approximately 40 kb Bin1 gene has been determined [SEQ ID NO: 6]. More detailed discussion of the Bin1 genomic sequence is provided in Example 3. The exon-intron junction sequences derived are desirable for applying PCR technology to identify mutations in DNA derived from tumor biopsies, using techniques similar to those applied to sequences derived from other tumor suppressor genes (e.g., p53 and BRCA1). The sequenced region of the Bin1 gene spans regions previously found to be rearranged in liver and cervix carcinoma cell lines, making it possible to map deletions and possible mutations in primary human tumor DNA by PCR technology. Using the genomic clones, the human Bin1 gene has been mapped to chromosome 2q14, a region frequently deleted in prostate carcinoma and in radiation-induced malignancies.

These nucleic acid sequences are useful for a variety of diagnostic and therapeutic uses. Advantageously, the nucleic acid sequences are useful in the development of diagnostic probes and antisense probes for use in the detection and diagnosis of conditions characterized by deregulation or amplification of c-myc. The nucleic acid sequences of this invention are also useful in the production of mammalian, and particularly, murine and human Bin1 proteins.

II. Protein Sequences

The present invention also provides mammalian Bin1 polypeptides or proteins. These proteins are free from association with other contaminating proteins or materials with which they are found in nature. In one embodiment, the invention provides a partial murine Bin1 [SEQ ID NO:2]

polypeptide of 135 amino acids having a predicted molecular weight (MW) of 13,688. In another embodiment, the invention provides a full-length human Bin1 [SEQ ID NO:4] of 451 amino acids with an estimated MW of 50,048. The apparent MW of human Bin1 on sodium dodecyl sulfate polyacrylamide (SDS-PA) gels is approximately 70 kD. Data provided herein shows that the Bin1 DNA encodes a nuclear protein which is identical to a protein found in normal human fibroblasts.

Further encompassed by this invention are fragments of the Bin1 polypeptides. Such fragments are desirably characterized by having Bin1 biological activity, including, e.g., the ability to interact with c-Myc. These fragments may be designed or obtained in any desired length, including as small as about 8 amino acids in length. Such a fragment may represent an epitope of the protein. One particularly desirable fragment is located at amino acid residues 270–383 of SEQ ID NO: 4, which is the c-Myc binding domain (MBD). Another desirable fragment is located at residues 378–451 of SEQ ID NO: 4 and is a Src homology 3 (SH3) domain. A third fragment is located at residues 223–251 of SEQ ID NO:4 and includes the T antigen/RED1/p93dis1 motifs discussed herein. Yet another desirable fragment includes the BAR domain, located at amino acid residues 1–222 of SEQ ID NO:4. Finally, a fragment containing the nuclear localization domain located at amino acid residues 252 to about 265 of SEQ ID NO: 4, may also be desirable.

Also included in the invention are analogs, or modified versions, of the proteins provided herein. Typically, such analogs differ by only one to four codon changes. Examples include polypeptides with minor amino acid variations from the illustrated amino acid sequences of Bin1 (FIGS. 1 and 2; SEQ ID NO:2 and 4); in particular, conservative amino acid replacements. Conservative replacements are those that take place within a family of amino acids that are related in their side chains and chemical properties. Also provided are homologs of the proteins of the invention which are characterized by having at least 85% homology with SEQ ID NO:2 or SEQ ID NO:4. It has previously determined that the murine and human Bin1 (in partial) are about 88.5% identical.

Further included in the invention are homologs of Bin1. Based on the sequence information provided herein, one of skill in the art can readily obtain Bin1 from other mammalian species. Such homologs are typically at least 85% homologous with SEQ ID NO: 2 or SEQ ID NO: 4.

Additionally, the Bin1 proteins [SEQ ID NO:2 and 4] of the invention may be modified, for example, by truncation at the amino or carboxy termini, by elimination or substitution of one or more amino acids, or by any number of now conventional techniques to improve production thereof, to enhance protein stability or other characteristics, e.g. binding activity or bioavailability, or to confer some other desired property upon the protein.

III. Expression

A. In Vitro

To produce recombinant Bin1 proteins of this invention, the DNA sequences of the invention are inserted into a suitable expression system. Desirably, a recombinant molecule or vector is constructed in which the polynucleotide sequence encoding Bin1 is operably linked to a heterologous expression control sequence permitting expression of the murine or human Bin1 protein. Numerous types of appropriate expression vectors are known in the art for mammalian (including human) protein expression, by standard molecular biology techniques. Such vectors may be selected from among conventional vector types including insects, e.g., baculovirus expression, or yeast, fungal, bacterial or viral expression systems. Other appropriate expression vectors, of which numerous types are known in the art, can also be used for this purpose.

Methods for obtaining such expression vectors are well-known. See, Sambrook et al, *Molecular Cloning. A Laboratory Manual*, 2d edition, Cold Spring Harbor Laboratory, New York (1989); Miller et al, *Genetic Engineering*, 8:277–298 (Plenum Press 1986) and references cited therein.

Suitable host cells or cell lines for transfection by this method include mammalian cells, such as Human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, production, and purification are known in the art. [See, e.g., Gething and Sambrook, *Nature*, 293.:620–625 (1981), or alternatively, Kaufman et al, *Mol. Cell. Biol.*, 5(7):1750–1759 (1985) or Howley et al, U.S. Pat. No. 4,419,446].

Similarly bacterial cells are useful as host cells for the present invention. For example, the various strains of *E. coli* (e.g., HB101, MC1061, and strains used in the following examples) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the polypeptides of the present invention. Other fungal cells may also be employed as expression systems.

Alternatively, insect cells such as *Spodoptera frugipedera* (Sf9) cells may be used.

Thus, the present invention provides a method for producing a recombinant Bin1 protein which involves transfecting a host cell with at least one expression vector containing a recombinant polynucleotide encoding a Bin1 protein under the control of a transcriptional regulatory sequence, e.g., by conventional means such as electroporation. The transfected host cell is then cultured under conditions that allow expression of the Bin1 protein. The expressed protein is then recovered, isolated, and optionally purified from the culture medium (or from the cell, if expressed intracellularly) by appropriate means known to one of skill in the art.

For example, the proteins may be isolated in soluble form following cell lysis, or may be extracted using known techniques, e.g., in guanidine chloride. If desired, the Bin1 proteins of the invention may be produced as a fusion protein. For example, it may be desirable to produce Bin1 fusion proteins, to enhance expression of the protein in a selected host cell, to improve purification, or for use in monitoring the presence of Bin1 in tissues, cells or cell extracts. Suitable fusion partners for the Bin1 proteins of the invention are well known to those of skill in the art and include, among others, β-galactosidase, glutathione-S-transferase, and poly-histidine.

B. In Vivo

Alternatively, where it is desired that the Bin1 protein be expressed in vivo, e.g., for gene therapy purposes, an appropriate vector for delivery of Bin1, or fragment thereof (such as the SH3 domain), may be readily selected by one of skill in the art. Exemplary gene therapy vectors are readily available from a variety of academic and commercial sources, and include, e.g., adeno-associated virus

[International patent application No. PCT/US91/03440], adenovirus vectors [M. Kay et al, *Proc. Natl. Acad. Sci. USA*, 91:2353 (1994); S. Ishibashi et al, *J. Clin. Invest.*, 92:883 (1993)], or other viral vectors, e.g., various poxviruses, vaccinia, etc. Methods for insertion of a desired gene, e.g. Bin1, and obtaining in vivo expression of the encoded protein, are well known to those of skill in the art.

IV. Antisera and Antibodies

The Bin1 proteins of this invention are also useful as antigens for the development of anti-Bin1 antisera and antibodies to Bin1 or to a desired fragment of a Bin1 protein. Specific antisera may be generated using known techniques. See, Sambrook, cited above, Chapter 18, generally, incorporated by reference. Similarly, antibodies of the invention, both polyclonal and monoclonal, may be produced by conventional methods, including the Kohler and Milstein hybridoma technique, recombinant techniques, such as described by Huse et al, *Science*, 246:1275–1281 (1988), or any other techniques known to the art. For example, rabbit polyclonal antisera was developed and recognizes an epitope(s) between amino acid residues 190–250 of SEQ ID NO: 4. This antisera has been found to be human-specific. Since amino acids 190–250 are outside the MBD and SH3 domain, for experimental needs two additional antisera have been raised to these regions. The immunogens included human Bin1 amino acids 270–383 (MBD) [SEQ ID NO: 4] or amino acids 378–451 (SH3) [SEQ ID NO: 4]. Each antisera has been shown to recognize the appropriate domain by immunoprecipitation.

Additionally, six (6) Bin1-specific monoclonal antibodies, termed 99-D through 99-I, have been characterized. The approximate location of the epitopes within Bin1 for each antibody has been mapped. MAb 99D recognizes an epitope within amino acids 190–250 [SEQ ID NO: 4]; MAbs 99F–99I recognize epitopes within the NLS (amino acids 252–261 [SEQ ID NO: 4]); MAb 99E recognizes a complex epitope requiring amino acids 190–250 and amino acids 263–397 [SEQ ID NO: 4]. Each antibody has been isotyped and demonstrated to work in immunoprecipitation, Western blotting, and immunohistochemistry methodology. Particularly, MAb 99D and MAb 99F are IgG2b isotypes; MAbs 99E, 99G and 99H are IgG1 isotypes. Further, MAbs 99D and 99F have been determined to be useful for immunohistochemistry with sectioned biopsy tissue and tissue culture cells, and are therefor likely to be useful for clinical applications to analyze tumor biopsies. MAb 99D recognizes a nuclear protein present in all normal cells examined so far but missing in carcinoma cells previously demonstrated to lack Bin1 RNA. 99F has been determined to specifically recognize a cytoplasmic form of Bin1 which is induced following muscle differentiation in an in vitro model system which is described below. MAb 99D recognizes both the cytoplasmic as well as the nuclear forms of Bin1 and has been determined to be effective for detecting Bin1 protein by standard Western methodology in nonionic detergent lysates of a wide variety of tissues and tissue culture cells. MAbs 99D and 99F have been shown to recognize both murine and human Bin1 polypeptides.

Also encompassed within this invention are humanized and chimeric antibodies. As used herein, a humanized antibody is defined as an antibody containing murine complementary determining regions (CDRs) capable of binding to Bin1 or a fragment thereof, and human framework regions. These CDRs are preferably derived from a murine monoclonal antibody (MAb) of the invention. As defined herein, a chimeric antibody is defined as an antibody containing the variable region light and heavy chains, including both CDR and framework regions, from a Bin1 MAb of the invention and the constant region light and heavy chains from a human antibody. Methods of identifying suitable human framework regions and modifying a MAb of the invention to contain same to produce a humanized or chimeric antibody of the invention, are well known to those of skill in the art. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994). Other types of recombinantly-designed antibodies are also encompassed by this invention.

Further provided by the present invention are anti-idiotype antibodies (Ab2) and anti-anti-idiotype antibodies (Ab3). Ab2 are specific for the target to which anti-Bin1 antibodies of the invention bind and Ab3 are similar to Bin1 antibodies (Ab1) in their binding specificities and biological activities [see, e.g., M. Wettendorff et al., "Modulation of anti-tumor immunity by anti-idiotypic antibodies." In *Idiotypic Network and Diseases*, ed. by J. Cerny and J. Hiernaux J, Am. Soc. Microbiol., Washington DC: pp. 203–229, (1990)]. These anti-idiotype and anti-anti-idiotype antibodies may be produced using techniques well known to those of skill in the art. Such anti-idiotype antibodies (Ab2) can bear the internal image of the c-Myc and bind to it in much the same manner as Bin1 and are thus useful for the same purposes as Bin1.

In general, polyclonal antisera, monoclonal antibodies and other antibodies which bind to Bin1 as the antigen (Ab1) are useful to identify epitopes of Bin1, to separate Bin1 from contaminants in living tissue (e.g., in chromatographic columns and the like), and in general as research tools and as starting material essential for the development of other types of antibodies described above. Anti-idiotype antibodies (Ab2) are useful for binding c-Myc and thus may be used in the treatment of cancers in which c-Myc is part of a biochemical cascade of events leading to tumor formation. The Ab3 antibodies may be useful for the same reason the Ab1 are useful. Other uses as research tools and as components for separation of c-Myc from other contaminant of living tissue, for example, are also contemplated for these antibodies.

V. Diagnostic Reagents and Methods

Advantageously, the present invention provides reagents and methods useful in detecting and diagnosing abnormal levels of Bin1, and particularly deficiencies or excess production thereof, in a patient. As defined herein, a deficiency of Bin1 is an inadequate amount of Bin1 to compensate for the levels of c-Myc in a patient. Conditions associated with deficiencies of Bin1 include a variety of cancers, e.g., breast cancer, liver cancer and colon cancer, and hyperplastic disease states, e.g., benign prostate hyperplasia.

Thus, the proteins, protein fragments, antibodies, and polynucleotide sequences (including anti-sense polynucleotide sequences and oligonucleotide fragments), and Bin1 antisera and antibodies of this invention may be useful as diagnostic reagents. These reagents may optionally be labelled using diagnostic labels, such as radioactive labels, colorimetric enzyme label systems and the like conventionally used in diagnostic or therapeutic methods. Alternatively, the N- or C-terminus of Bin1 or a fragment thereof may be tagged with a viral epitope which can be recognized by a specific antisera. The reagents may be used to measure abnormal Bin1 levels in selected mammalian tissue in conventional diagnostic assays, e.g., Southern blotting, Northern and Western blotting, polymerase chain reaction (PCR), reverse transcriptase (RT) PCR, immunostaining, and the like. For example, in biopsies of tumor tissue, loss of Bin1 expression in tumor tissue could be directly verified by RT-PCR or immunostaining. Alternatively, a Southern analysis, genomic PCR, or fluorescence in situ hybridization (FISH) may be performed to confirm Bin1 gene rearrangement.

In one example, as diagnostic agents the polynucleotide sequences may be employed to detect or quantitate normal Bin1. The selection of the appropriate assay format and label system is within the skill of the art and may readily be chosen without requiring additional explanation by resort to the wealth of art in the diagnostic area.

Thus the present invention provides methods for the detection of disorders characterized by insufficient Bin1 levels. Currently, it is anticipated that antibodies of the invention, such as MAbs 99D and 99F, which have been found to be able to withstand the conditions necessary for tissue fixation, will be particularly useful for biopsies. However, the protein, antibody, antisera or polynucleotide reagents of the invention are expected to be similarly useful in the following methods. The methods involve contacting a selected mammalian tissue, e.g., a biopsy sample or other cells, with the selected reagent, protein, antisera antibody or DNA sequence, and measuring or detecting the amount of Bin1 present in the tissue in a selected assay format based on the binding or hybridization of the reagent to the tissue.

VI. Therapeutic Compositions and Methods

Compositions and methods useful for the treatment of conditions associated with inadequate Bin1 levels are provided. As stated above, included among such conditions are liver, colon and breast cancers and hyperplastic disease states. Also provided are compositions and methods for inhibiting Bin1 activity in order to ameliorate a condition in which apoptosis is activated and Bin1 plays a role. Such conditions may include degenerative conditions, e.g., neurodegenerative diseases.

The therapeutic compositions of the invention may be formulated to contain an anti-idiotype antibody of the invention, the Bin1 protein itself or a fragment thereof. The therapeutic composition desirably contains 0.01 µg to 10 mg protein. Such a composition may contain the Bin1 SH3 domain (amino acids 378–451 of SEQ ID NO: 4) and be administered to mimic the effect of normal Bin1 and bind c-Myc, thereby preventing its cancer causing function. These compositions may contain a pharmaceutically acceptable carrier. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

Still another method involves the use of the Bin1 polynucleotide sequences for gene therapy. In the method, the Bin1 sequences are introduced into a suitable vector for delivery to a cell containing a deficiency of Bin1 and/or to block tumor growth. By conventional genetic engineering techniques, the Bin1 gene sequence may be introduced to mutate the existing gene by recombination or to replace an inactive or missing gene.

Generally, a suitable polynucleotide-based treatment contains between $1 \times 10^{-3}$ pfu to $1 \times 10^{-12}$ pfu per dose. However, the dose, timing and mode of administration of these compositions may be determined by one of skill in the art. Such factors as the age, condition, and the level of the Bin1 deficiency detected by the diagnostic methods described above, may be taken into account in determining the dose, timing and mode of administration of the therapeutic compositions of the invention. Generally, where treatment of an existing cancer or hyperplastic state is indicated, a therapeutic composition of the invention is preferably administered in a site-directed manner and is repeated as needed. Such therapy may be administered in conjunction with conventional therapies, including radiation and/or chemotherapeutic treatments.

The following examples illustrate the isolation and use of the Bin1 sequences of the invention. These examples are illustrative only and do not limit the scope of the invention.

Example 1

Identification and Characterization of Bin1

A. Murine Bin1 cDNA

A yeast two hybrid approach [Fields, S. and O. Song., *Nature*, 340:245–6 (1989)] was used to screen for Myc-interacting proteins (Bin1) in a murine embryo E10.5 cDNA library. The cDNA library was derived from day 10.5 mouse embryonic RNA [A. B. Vojtek et al, *Cell*, 74:205–214 (1993)]. This system takes advantage of the modular nature of transcription factors, whose DNA-binding and transcriptional activating components can be assembled in trans by interacting protein (IP) domains derived from other polypeptides. A previously described two hybrid system [Vojtek et al, cited above] and a 16 amino acid nontransactivating polypeptide derived from the human c-Myc "Myc box 1" (MB1) region [Prendergast, G. C. and E. B. Ziff, *Trends in Genet.*, 8:91–96.3 (1992)] EDIWKKFELLPTPPLS (human c-Myc amino acids 47–62) [SEQ ID NO:5], were used as "bait" in the screen.

Briefly, the "bait" plasmid contained a TRP1 marker and a LexA-MB1 fusion protein as the DNA binding component, and the cDNA library vector, pVP16, contained a LEU2 marker and the herpes simplex virus VP16 protein as the transcriptional transactivator fused to the cDNA library inserts. cDNA synthesized from the 10.5 day murine embryo RNA was size-selected by random DNaseI treatment to ~0.05 kb, treated with Klenow enzyme, NotI linked, and subcloned into pVP16. This cDNA library was designed to express protein modules whose interactions might be occluded in full-length polypeptides. The yeast strain L40 (MATa trp1–901 leu2–3,112 LYS2::(lexAop)4-HIS3 URA3::(lexAop)8-lacZ) served as the host for the two hybrid screen [see, Vojtek et al, cited above].

An L40 derivative expressing the MB1 "bait" was transfected with the cDNA library and approximately $3 \times 10^7$ TRP+LEU+ transformants were examined in the primary screen, 300–400 of which were also the HIS+LacZ+ phenotype, which is diagnostic for interaction between the "bait" and library components [Vojtek et al, cited above]. The clones were cured of the original "bait" plasmid by standard methods [Guthrie, C. and G. R. Fink, eds., Guide to Yeast Genetics and Molecular Biology, *Meth. Enzymol.*, 194, Academic Press: New York (1991)]. One hundred clones cured of the bait plasmid were tested for interaction by a mating strategy with a set of test baits.

The test "baits" included the original lexA-MB1 peptide construct, a set of negative controls that included no insert, lamin [A. B. Vojtek et al, *Cell*, 74:205–214 (1993)], the small GTP-binding protein RhoB [D. Jahner, *Mol. Cell. Biol.*, 11:3682–3690 (1991)], the peptide FTRHPPVLTPP-DQEVI [SEQ ID NO: 7] derived from rat protein kinase Cβ2, a mutant MB1 peptide, a similarly sized but nonspecific peptide derived from protein kinase C, or lamin. The protein kinase C (PKC) peptide contained a phosphorylation site structurally analogous to the MB1 T58 phosphorylation site, which is recognized by glycogen synthase kinase-3 (GSK-3), a kinase present in yeast. The PKC peptide was designed to control for binding proteins that might non-specifically interact with phosphooligopeptides (e.g., peptidases, kinases, phosphatases). MB1 specificity was reproducibly exhibited by 14/99 of the original yeast clones.

cDNA library plasmids were shuttled from the desired clones to *E. coli* [Guthrie et al. cited above] and the DNA sequence of the inserts was determined. All clones contained related or identical sequences of approximately 0.4 kb containing an open reading frame (ORF) of 135 amino acids encoding a Myc-interacting polypeptide, termed Bin1 [SEQ ID NO:2], which exhibited specificity for Myc.

B. Bacterial Expression of murine Bin1 polypeptide [SEQ ID NO:2] as a soluble GST fusion protein To study the association of the 135 aa murine Bin1 polypeptide [SEQ ID NO:2] with Myc in vitro, the ~0.4 kb cDNA [SEQ ID NO:1] was expressed as a glutathione-S-transferase (GST) fusion protein and used in binding assays with $^{35}$S-methionine-labeled in vitro translated (IVT) proteins. The binding experiments were configured essentially as described in A. K. Rustgi et al. *Nature*, 352:541–544 (1991).

To construct the GST fusion protein, the murine cDNA insert on a ClaI-EcoRI fragment was substituted for a similar fragment in pE47 [C. Murre et al. *Cell*, 56:777–783 (1989)], making pATG-99. The pATG-99 ORF included an initiator methionine, added a 15 amino acid N-terminal extension (3 amino acids from E47 and 12 amino acids from VP16) to the 135 residue clone #99 ORF, and retained the translational termination site derived from the two hybrid vector. Expression of the ATG99 polypeptide was confirmed by in vitro translation from pATG-99. The pATG-99 insert was then subcloned into pGEX-2T (Pharmacia) and the recombinant plasmid introduced into *E. coli*. GST-99 polypeptide was expressed and purified from *E. coli* cell extracts on glutathione-Sepharose (Pharmacia), using protocols supplied by the vendor.

Twenty (20) μl (~0.5 μg) of purified GST-99 protein was analyzed on an SDS-PA gel fixed and stained with Coomassie Blue. The apparent molecular weight (MW) of the Bin1 component of the fusion (22 kD) is larger than the predicted MW (14 kD) but is consistent with the apparent MW of in vitro translated murine Bin1 [SEQ ID NO: 2].

C. In Vitro Association of Myc and Bin1 [SEQ ID NO: 2]

[$^{35}$S]-methionine labeled c-Myc polypeptides were generated by IVT using TNT rabbit reticulocyte lysates (Promega). Expression plasmids included CMV Hm [G. C. Prendergast et al. *Cell*, 65:395–407 (1991)]; CMV Hm subclones containing MB1 deletion amino acids 49–101 [J. Stone et al. *Mol. Cell. Biol.*, 7:1697–1709 (1987)]; MB2 deletion amino acids 120–140 [L. Li et al. *EMBO J.*, 13:4070–4079 (1994)], or both deletions; the adenovirus E1A vectors p12S, p13S; and the SV40 large T antigen vector pTag [unpublished data]; and CMV-USF [L. Li, cited above].

Approximately 2.5 μg of GST or GST-99 and 10 μl of an IVT reaction were added to 0.5 ml binding buffer (10 mM TrisCl pH 7.5, 5 mM EDTA, 500 mM NaCl, 0.25% NP40) incubated 1 hr at 4° C. on a nutator shaker, washed four times with binding buffer, and analyzed by SDS-PAGE and fluorography. c-Myc (but none of the other polypeptides produced by IVT) exhibited association with GST-99.

D. Association of Bin1 [SEQ ID NO:2] with TBP but not USF

[$^{35}$S]-labeled TBP and USF were generated by IVT and tested for GST-99 binding as in C. above. Reinforcing the notion that it might be involved in MB1 function in transcriptional regulation by Myc, Bin1 bound to TATA-binding protein [TBP, a critical component of the basal transcription apparatus]. Other polypeptides that were tested for GST-99 interaction and found to be negative included Max, cell cycle protein p107, transcription factor YY1, extracellular protein PAI-1, small GTP-binding protein RhoB, and empty-vector-associated products. Taken together, these findings argued that the association between GST-99 and Myc was both specific and physiologically relevant, since it depended upon the presence of the Myc boxes.

Example 2

Isolation of Human Bin1 cDNA

BLAST searches of the complete DNA sequence database [GenBank] with the murine Bin1 sequence showed no strong similarities to known genes, but revealed an approximately 89% identity to an 289 bp uncharacterized human "expressed sequence tag". This finding suggested that Bin1 represented a novel gene conserved and expressed in humans.

Northern analysis of RNA from several human tissues using a murine Bin1 cDNA [SEQ ID NO: 1] as probe revealed a single RNA species of ~2.2 kb that was abundant in skeletal tissue. A 1.95 kilobase human Bin1 cDNA was obtained from a human skeletal muscle λZAPII cDNA library (Stratagene, La Jolla, Calif.) by standard methods [Sambrook et al. cited above], using the murine Bin1 probe, i.e., by hybridization with [$^{32}$P]-labeled clone #99 insert and washing under low stringency conditions (2×SSC 42° C.). The complete sequence of this ~2.0 kb full-length cDNA, p99f, was determined [SEQ ID NO: 3] using the dideoxy method with Sequenase (US Biochemicals) and assembled and analyzed with MacVector software (IBI/Kodak). DNA database comparisons were performed using BLAST software. The subcloned cDNA contained a 451 amino acid ORF of predicted MW 50049 which included a nuclear localization signal (NLS), a Src homology 3 (SH3) domain, and a central region of approximately 89% identity to clone #99 which was implicated as the Myc-interacting region. The predicted gene product was termed Bin1 for Box-dependent Myc-Interacting protein-1 [SEQ ID NO:4].

Plasmid p99f was deposited with the American Type Culture Collection, 12301 Parklawn Drive, Rockville, Md. 20852 USA. This deposit was made on Dec. 12, 1996 pursuant to the provisions of the Budapest Treaty, and bears the ATCC Designation 97823.

Comparisons of the Bin1 amino acid sequence to the DNA database were performed using the search algorithm BLAST [S. F. Altschul et al. *J. Mol. Biol.*, 215:403–410 (1990)]. Using the complete sequence to search the database, two known genes were identified which had highly significant similarity to the terminal regions of Bin1 (p<10$^{-}$8). The first gene was amphiphysin, a neuronal protein of unknown function which is the putative autoimmune antigen in breast cancer-associated Stiff-Man syndrome [F. Folli et al. *N. Eng. J. Med.*, 328:546–551 (1993)], a paraneoplastic disorder that clinically presents in a fraction of breast cancer patients. The meaning of this relationship was unclear but suggested connections of Bin1 to cancer. The second gene was RVS167, a negative regulator of the cell division cycle in *S. cerevisiae*. The region of the most extensive similarity between amphiphysin and RVS167, approximately 50% and 25%, respectively, lies within residues 1–222 of Bin1 [SEQ ID NO:4]. Therefore, this N-terminal region of Bin1 has been termed herein the BAR domain (for Bin1/amphiphysin/RVS167-related domain). These BAR-containing proteins all contained C-terminal SH3 domains that were separated from the BAR domains by sequences unique to each protein. The extensive similarity of the BAR domains in these proteins suggest a common molecular function. Moreover, the relationship suggests roles for Bin1 in breast malignancy, where Myc is frequently involved, and in cell cycle regulation. Finally, since RVS167 is a negative regulator which is dispensable for cell growth but required for cell cycle exit, the similarity to RVS167 would be consistent with the likelihood that Bin1 is a tumor suppressor, which is similarly dispensible for cell growth.

To gain additional insights into the molecular functions of Bin1, additional BLAST searches were performed with subsections of the Bin1 sequence. These searches identified several gene products which all function in regulation of cell cycle transit and/or chromosomal structure. Several additional relationships were revealed within the Bin1 BAR domain. These included pericentrin (30% identical; 46% similar; P<0.01), a centromere-binding protein required for proper chromosome organization during the cell cycle M phase; mitosin (24% identical; 48% similar; P=0.02), a protein implicated in transit through M phase; and SMC1 (21% identical; 43% similar; P=0.05), a yeast regulator of M phase chromosome segregation. In the scoring range where these similarities were observed, highly alpha helical regions of non-muscle myosin, tropomyosin, and the trp gene product were also found, suggesting that the BAR domain shares their highly helical structure. Between the C-terminal end of the BAR region and the nuclear localization signal (NLS; amino acids 252–265, SEQ ID NO: 4) lies an additional Bin1 domain (amino acids 224–251, SEQ ID NO: 4), encoded by a single exon, which is not found in amphiphysin and RVS167 but which also contains motifs seen in proteins controlling cell cycle and chromosome structure. One ~10 amino acid motif is found in a functionally important region of the SV40 T antigen oncoprotein, while a second motif is seen in RED1, a yeast protein implicated in chromosome segregation. Proximal to these motifs is an additional motif which is similar to p93dis1, another yeast protein implicated in chromosome segregation. Taken together, these observations strengthen the likelihood that Bin1 participates in some aspect of cell cycle regulation and further suggests a role in chromosome structure control.

Example 3

Human Bin1 Gene Isolation, Structure and Regulation

A. DNA sequencing of the human Bin1 gene

Genomic clones of human Bin1 have been obtained. A 40 Kb contiguous sequence composed of five lambda phage genomic inserts has been assembled which contains the entire Bin1 gene. Approximately 15 kb of the gene sequence is provided in SEQ ID NO: 6. Eight contiguous exons from the C-terminal BAR region to the SH3 domain have been identified. Three additional N-terminal BAR exons have also been identified. Five other exons identified by DNA sequence analysis algorithms appear in alternatively spliced RNAs found to be expressed exclusively in brain. With reference to the features information provided with respect to SEQ ID NO: 6, the nine exon sequences correspond to the following Bin1 cDNA sequences [SEQ ID NO: 3]: 623–655 (partial sequence of BAR region exon); 656–731 (3' BAR region exon); 732–814 (U1 region exon); 815–859 (NLS); 860–1004 (U2 region exon); 1005–1094 (5' MBD region exon); 1095–1205 (3' MBD region exon); 1206–1307 (5' SH3 domain region exon); 1308–1925 (3' SH3 domain/3' untranslated region [UTR] exon).

Using the genomic clones, the human Bin1 gene has been mapped to chromosome 2q14. This region is within a mid-2q locus that has been reported to be deleted in approximately 50% of metastatic prostate carcinomas. The region of the murine genome syntenic to human 2q14 has also been reported to be deleted in >90% of radiation induced leukemias and lymphomas. These data strengthen the previous assertion that Bin1 may be encoded by a novel tumor suppressor gene.

B. Increase in Bin1 Levels During Muscle and Neuronal Differentiation

Bin1 RNA has been found to be present in brain and muscle cells at 10- to 100-fold higher levels than other tissues, a feature shared with cell cycle kinase inhibitors (CKIs). Since these cells are postmitotic and Bin1 had been shown to block Myc's ability to induce cell cycle progression, it is possible that upregulation of Bin1 has a role in cell cycle exit associated with cell differentiation. To begin to assess this possibility, Bin1 expression was examined using in vitro model systems for differentiation of muscle cells (murine C2C12 premyoblast cells) [L. Silberstein et al, Cell, 46:1075–1081 (1986)] and neurons (rat PC12 pheochromocytoma cells) [L. A. Greene and A. S. Tischler, Proc. Natl. Acad. Sci. USA, 73:2424–2428 (1976)].

This analysis revealed that both Bin1 RNA and protein are regulated during cell differentiation. Bin1 RNA levels were increased following induction of cell differentiation in C2C12 or PC12 cells, by serum deprival or nerve growth factor (NGF) addition, respectively. In untreated PC12 cells, three transcripts of ~1.3, ~2.4, and ~2.9 kb were noted. Within 5 days of NGF treatment the level of the ~2.9 kb RNA was increased several-fold, concomitant with neurite extension, while the level of the other two RNAs decreased to undetectable levels. The nature of the ~1.2 kb transcript, which was most abundant in untreated cells, was unclear but its unusually small size suggested the possibility that it was truncated due to mutation (PC12 was derived from a rat adrenal gland tumor). In C2C12 cells, a single ~2.4 kb transcript noted increased ~20-fold within 5 days of serum deprival, concomitant with myotube formation. These observations suggest that Bin1 may be involved in cell cycle regulation during neuronal and muscle cell differentiation.

C. Identification of a larger Bin1 Polypeptide in Differentiated Muscle Cells

Western analysis with the 99D MAb confirmed an increase in Bin1 expression and revealed the presence of a slightly larger Bin1 polypeptide generated 3 days post-induction. Levels of the smaller Bin1 polypeptide detected in undifferentiated cells was found to remain constant while the larger species increased dramatically. Indirect immunofluorescence using 99D antibody was used to examine the cell localization of Bin1 during C2C12 differentiation. Bin1 staining was found to change from a strictly nuclear pattern to whole cell pattern including the cytoplasm. The 99F antibody was found to detect only the larger polypeptide and stain only the cytoplasm (did not stain the nuclear protein). Thus, the larger Bin1 polypeptide induced during differentiation is completely confined to the cytoplasm.

Example 4

Construction of Mammalian Expression Vectors and Immunoprecipitation Techniques Viral vectors for delivering Bin1 into insect, rodent and human cells have been developed for various purposes.

including therapeutic purposes and to permit high-level Bin1 protein production and efficient gene transfer.

A. Baculoviral Vector

~1.6 kb EcoRI fragment containing the complete Bin1 coding region was inserted into the baculovirus recombination vector pVL1393 (Invitrogen, Inc., San Diego, Calif.), generating pBacBin. Sf9 insect cells were cotransfected with pBacBin and a plasmid encoding a defective baculovirus which cannot propagate. Rare recombination between these two plasmids in vivo leads to generation of a lytic recombinant baculovirus which can be propagated. Virus produced in cultures of cotransfected cells was propagated in mass Sf9 culture. Bin1 production was verified by Western analysis of NP40 lysates prepared 24 and 48 hr after infection of Sf9 cells infected with the BacBin virus, using 99D monoclonal antibody.

B. Adenoviral vector

The strategy and plasmid vector systems to produce recombinant adenovirus has been described [K. Kozarsky et al, Curr. Opin. Genet. Dev., 3:499–503 (1993)]. Similar to the approach taken to make baculoviral vectors, two plasmids are used which contain complementary regions which can homologously recombine in vivo. Recombinant virus is produced only in transfected cells where recombination has taken place. The plasmid pAdCMVpAT153 is used to introduce the gene of interest. pAdCMVpAT153 contains the left 6% of the adenovirus serotype 5 genome, modified such that the E1 region is replaced with a cytomegalovirus (CMV) early region enhancer/promoter, multiple cloning site, and a G418 resistance gene cassette. Included in the cell transfection with this vector is a ~34 kb ClaI-digested fragment of adenovirus type 5 DNA that includes the remainder of the adenoviral genome. This fragment contains a mutation in the E3 region which ablates the immune response in adenovirus-infected animals [T. Ranheim et al, J. Virol., 67:2159–2167 (1993)]. This feature was incorporated into the recombinant virus to increase the persistence and therefore the potential efficacy of Bin1-based gene therapy approaches. The cell host for transfection is human 293 cells, an epithelial line which expresses the E1 region gene products required for propagation of recombinant adenoviruses.

The plasmid pAdenoBin was generated by inserting a ~1.6 kb EcoRI fragment containing the complete Bin1 coding region into the multiple cloning site of pAdCMV-pAT153. 293 cells cotransfected with pAdenoBin and the ClaI-digested adenoviral DNA fragment were subjected to G418 selection and screening and purification by plaque assay (recombinant viruses are lytic in 293 cells). DNA isolated from a Bin1 virus identified in this manner will be validated by Southern analysis to confirm that the Bin1 cDNA is intact.

These vectors are particularly well suited for use in human therapies.

C. Moloney retrovital vector

A recombinant Bin1 retrovirus was generated using methods that have been described [N. Landau et al, J. Virol., 66:5110–5113 (1992)]. The Bin1 plasmid vector pSRαMSV-Bin1 was generated by inserting the ~1.6 kb EcoRI fragment containing the complete Bin1 coding region into pSRαMSV, a retrovital vector that lacks RNA packaging signals and includes a G418 resistance gene cassette. Briefly, recombinant virus was isolated from the media of COS monkey cells cotransfected with pSRαMSV-Bin1 and pSVΨ-E-MLV, a proviral vector which provides the necessary retroviral packaging components. Recombinant virus was used to infect Rat1 fibroblasts and infected cell populations were selected by G418 selection. Expression of recombinant Bin1 in the Rat1 cell populations was confirmed by Northern and Western analysis.

Although the procedure above generated ecotropic Bin1 retroviruses limited to gene transfer to murine cells, those with skill in the art can easily generate amphotropic retroviruses that can transfer Bin1 to human cells. This is achieved by simply cotransfecting COS cells with pSRαMSV-Bin1 and pSVΨ-A-MLV, a packaging vector which encodes an amphotropic instead of ecotropic envelope glycoprotein [N. Landau et al, cited above]. An additional method is to transfect BING cells, an amphotropic human packaging cell line [W. Pear, G. Nolan, D. Baltimore, unpublished], with the Bin1 retroviral vector. Such vectors may be applied for use in gene therapies to attack human cancers.

D. Mammalian Expression Vectors

Bin1 mammalian cell expression vectors were constructed as follows and were used to generate the Bin1 proteins used in the following experiments. CMV-Bin1 was generated by subcloning a 1.6 kb EcoRI fragment from the full-length human Bin1 cDNA clone, p99f, that contained the entire predicted Bin1 coding sequence into pcDNA3 (Invitrogen), a mammalian cell expression vector that contains a cytomegalovirus enhancer/promoter and a 3' polyadenylation signal. CMV-HA-Bin1 was constructed by substituting a PvuII-EcoRI coding region fragment from CMV-Bin1 for an EcoRV-EcoRI fragment of neoCMV-hem rhoA, a RhoA expression plasmid that included an 8 residue N-terminal viral hemagglutinin (HA) epitope recognized by the monoclonal antibody 12CA5 [H. Niman et al, Proc. Natl. Acad. Sci. USA, 80.:4949–4953 (1983)]. The HA-Bin1 polypeptide created included residues 1–47 from the N-terminus of RhoA [Yeramian et al, Nucl. Acids Res., 15:1869 (1987)] and residues 52–451 of Bin1 [SEQ ID NO: 4]. This protein fusion added an N-terminal extension to Bin1 that allowed immunoprecipitation by anti-HA antibody 12CA5 [H. Niman et al, cited above]. CMV-Bin1ΔMBD deleted amino acid residues 270–377 [of SEQ ID NO: 4] in CMV-Bin1. It was constructed by ligating two separate PCR fragments generated by the 5' primer CCGGATCCGCGAT-GCTCTGGAACGTGGTGACG [nucleotides 60–80 of SEQ ID NO: 3] and the 3' primer GCGAATTCGTTGTCACT-GTTC TTCTTTCTGCG (fragment encoding aa 1–269) [nucleotides 866–842, corresponding to the antisense strand of SEQ ID NO: 3] and the 5' primer CGGAATTCAC-CATGGGTTTCATGTTC AAGGTACAG [nucleotides 1191–1211 of SEQ ID NO: 3] and the 3' primer CCGCTC-GAGTCATGGGACCCTCTCAGTGAAGTT (fragment encoding aa 378–451) [nucleotides 1415–1392, corresponding to the antisense strand of SEQ ID NO: 3]. This construction added the nonspecific amino acids EFTM at the fusion junction due to the restriction site added.

E. Immunoprecipitation

Two Bin1 antibodies were used in this study. A polyclonal antisera used was generated by immunizing rabbits with a GST fusion protein containing amino acid residues 189–398 of Bin1 (GST-99Pst) [SEQ ID NO: 4], that included all of the MBD, using a commercial service (Rockland, Inc., Boyerstown, Pa.). A Bin1-specific monoclonal antibody, 99D, was raised to the same immunogen as used for the polyclonal antiserum and is specific for the ~70 kD Bin1 polypeptide.

COS, MCF7, and IMR90 cells were cultured in Dulbecco's modified Eagle's media (DMEM) supplemented with 10% fetal bovine serum (Sigma) and 50 U/ml each penicillin and streptomycin (Fisher). Cells were transfected by a modified calcium phosphate protocol [C. Chen et al, *Mol. Cell. Biol.*, 7:2745–2752 (1987)] and metabolically labeled 48 hr later.

Ten microliters of crude antisera or prebleed sera was used for immunoprecipitations from IMR90 or transiently transfected COS cells metabolically labeled 2–4 hr in DMEM media lacking methionine and cysteine (Gibco) with 75–125 µCi/ml EXPRESS labeling reagent (NEN), washed with ice-cold phosphate-buffered saline, and extracted for 20 min on ice with RIPA buffer containing the protease inhibitors leupeptin, aprotinin, phenylmethylsulfonyl fluoride, and antipain [E. Harlow et al, Antibodies: A Laboratory Manual, Cold Spring Harbor Laboratory Press, Cold Spring Harbor, N.Y. (1988)]. Before the addition of Bin1 antibodies, extracts were precleared by centrifugation at 20,000 g for 15 min at 4° C. followed by 1 hr treatment with prebleed sera and 20 µl of a 1:1 slurry of protein G Sepharose beads at 4° C. on a nutator (Pharmacia). Precleared lysates were immunoprecipitated 90 min at 4° C. and then additional protein G beads were added and the incubation an additional 30 min. Beads were collected by brief centrifugation, washed four times with RIPA buffer, boiled in SDS gel loading buffer, fractionated on 10% gels, and fluorographed.

To establish that the Bin1 cDNA encoded a polypeptide similar to that found in normal cells, metabolically labeled extracts from IMR90 normal human diploid fibroblasts were subjected to immunoprecipitation. The results are described in Example 5 below.

Example 5

Characterization of Bin1

A polyclonal antiserum was raised to a bacterially-expressed polypeptide derived from the unique central region of Bin1, in order to reduce the chance of crossreaction with Bin1-related proteins. When incubated with metabolically labeled extracts from COS cells transfected with CMV-Bin1, this antisera immunoprecipitated two polypeptides with apparent MW 70 kD and 45 kD. All polypeptides were specifically recognized because their immunoprecipitation could be blocked by preincubating antisera with a molar excess of GST-Bin1 immunogen but not with unfused GST. In COS cells transfected with CMV-HA-Bin1, only the 70 kD polypeptide was immunoprecipitated by an anti-HA monoclonal antibody. The IVT product from the full-length cDNA also had an apparent mobility of 70 kD. These data indicated that the 70 kD species was Bin1 and suggested that the 45 kD species was a Bin1-related polypeptide. Cells transfected with CMV-Bin1ΔMBD, a Bin1 deletion construct lacking the central Myc-binding domain (amino acid 270–377 of SEQ ID NO: 4), exhibited stable accumulation of a polypeptide whose predicted and apparent MW were both 42 kD. This result indicated that full-length Bin1 migrated aberrantly due to an MBD determinant at 70 kD in SDS polyacrylamide gels, instead of at the predicted MW of 50 kD. Only the 45 kD polypeptide was detected in untransfected MCF7 breast tumor cells, which lacked Bin1 RNA, or in cells transfected with empty vector. Thus, the 45 kD species was not a coprecipitant or an alternately processed or degraded form of Bin1. Consistent with its assignment as a Bin1-related protein, the 45 kD polypeptide could be detected by Western blotting.

Example 6

Immunofluorescence Studies

~5×10³ HepG2 cells were seeded onto glass cover slips in 6 cm dishes and the next day transfected overnight with 4 µg CMV-Bin1 or pcDNA3. Two days later cells were washed and processed for immunofluorescence essentially as described [G. Prendergast et al, *EMBO J.*, 10:757–766 (1991)], using 5 µg of protein A Sepharose-purified anti-Bin1 IgG and a 1:1000 dilution of fluorescein-conjugated anti-rabbit IgG (Cappel) as the secondary antibody. Stained cover slips were examined and analyzed on a Leitz confocal microscope.

In this manner, cell localization was examined by indirect cell immunofluorescence of transiently transfected cultures of HepG2 hepatocarcinoma cells, which like MCF7 cells lack detectable Bin1 RNA (see below) and therefore provided an internal control for any crossreacting polypeptides. HepG2 cells transfected with CMV-Bin1 but not vector exhibited a speckled nuclear pattern of staining. This pattern of localization has been confirmed using the 99D monoclonal antibody in untransfected cells that express Bin1. The nuclear localization was consistent with the presence of a NLS in the primary sequence of Bin1 and with a nuclear site of interaction with Myc.

Example 7

Inhibition of Myc Oncogenic Activity by Bin1

As described herein, the ability of Bin1 to associate with Myc depended on the presence of MB1 and MB2, which are required for transformation activity [J. Stone et al, *Mol. Cell. Biol.*, 7:1697–1709 (1987); L. Li et al, *EMBO J.*, 13:4070–4079 (1994); and B. Pulverer et al, *Oncogene*, 9:59–70 (1994)]. The effects of Bin1 and the MBD deletion mutant Bin1ΔMBD (Example 4) on cell transformation were tested in the Ras cooperation assay [H. Land et al, *Nature*, 304:596–602 (1983)] performed in primary rat embryo fibroblasts (REFs; Whittaker Bioproducts). For specificity controls, additional experiments were performed in which Myc was replaced by either adenovirus E1A or SV40 T antigen, which can also cooperate with Ras in this assay. Since Myc mutants which cannot be phosphorylated at the MB1 T58 residue have been reported to escape p107-mediated inhibition of transactivation [A. T. Hoang et al, *Mol. Cell. Biol.*, 15:4031–4042 (1995)], the Myc T58M mutant was tested to see if it could escape any effects of Bin1. Since the original clone #99 cDNA was partial and encoded essentially only the MBD, it was anticipated that the clone #99 ORF might act in a dominant negative manner to interfere with either endogenous Bin1. Therefore, the effects of a clone #99 expression vector (Example 4) on Myc transformation were also tested.

The ~0.5 kb murine cDNA [SEQ ID NO: 1] engineered with a 5' Kozak initiator methionine from pATG-99 was subcloned into pcDNA3 (a CMV enhancer/promoter vaccine; Invitrogen, San Diego, Calif.) to generate neoCMV-ATG99. REF culture and transfection was performed essentially as described [G. Prendergast et al, *Genes Dev.*, 6:2429–2439 (1992)]. Briefly, secondary passage REFs seeded into 10 cm dishes were transfected overnight by a calcium phosphate coprecipitation method [C. Chen et al, cited above] with 5 µg each of the oncogene plasmids and 10 µg of other plasmids indicated, then passaged 1:5 the next day and fed with normal growth media until foci were scored by methanol fixation and crystal violet staining 12–14 days later. In some experiments, 0.5 mg/ml G418 was added the day after passaging. The following oncogene plasmids were used in REF assays. LTR Hm, which contains a Moloney long terminal repeat-driven normal human c-myc gene, and pT22, which contains an activated H-ras gene, have been described [H. Land et al, cited above and A. Kelekar et al,

*Mol. Cell. Biol.*, 6:7–14 (1986)]. LTR Hm T58M was generated by subcloning in LTR Hm a fragment containing the T58M mutation from the more potently transforming vector CMV Hm T58M [T. Born et al, *Mol. Cell. Biol.*, 14:5741–5747 (1994)]. A nontransforming Myc frameshift mutant (MycFS) was constructed by digestion of LTR Hm with a unique Bst EII in exon 2 of the human c-myc gene, filling with Klenow enzyme, and self ligation. The MycFS polypeptide encoded by this mutant, LTR Hm/Bst, is frameshifted at amino acid residue 104, eliminating its biological function. This frameshift mutant was included to establish that the augmentation of foci formation by CMV-ATG99 was Myc-dependent. In some control experiments, NeoCMV T and p1A/neo, encoding SV40 T antigen and adenovirus E1A, respectively, were substituted for LTR Hm. Transformed foci were scored two weeks later.

Figure 3B:
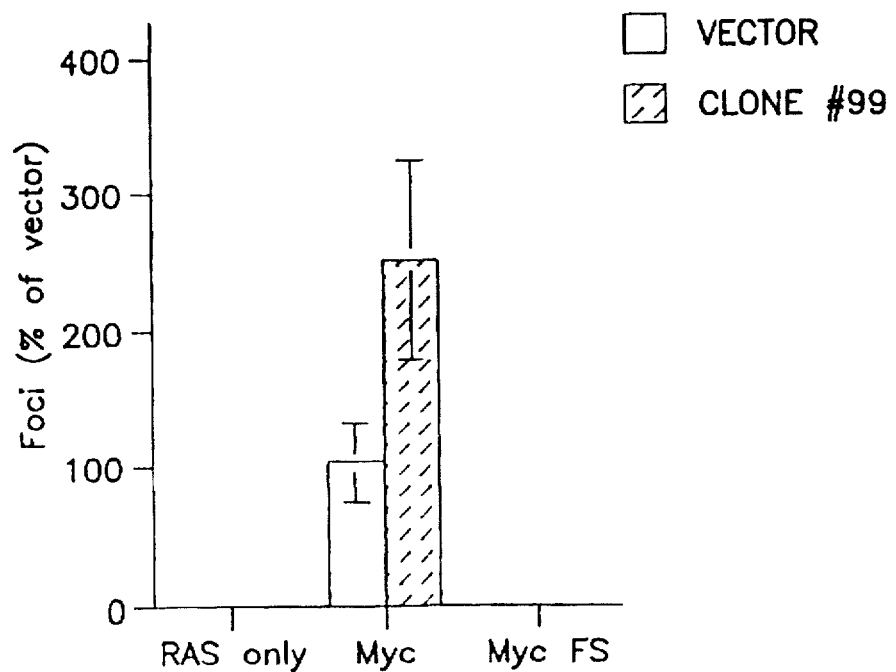
FIG. 3B is a bar chart illustrating the dominant inhibitory activity of MBD.

The results of the REF focus formation experiments are shown in FIG. 3. On its own or with activated ras, Bin1 lacked transforming activity. However, when cotransfected at a 2:1:1 ratio with myc and ras, Bin1 selectively inhibited focus formation ~7-fold. Inhibition could be titered by decreasing the ratio of Bin1 to myc and ras vectors in the transfected DNA (data not shown). Moreover, inhibition was dependent on Myc binding, since Bin1 ΔMBD, which lacks the Myc-binding domain, was inactive in this assay. The loss of inhibition could not be attributed to protein instability, because Bin1ΔMBD had been shown to stably accumulate in transfected COS cells, and could inhibit E1A transformation. In contrast to its effects on wild-type myc, bin1 did not efficiently inhibit transformation by myc T58M, even though this mutation did not affect binding (FIG. 3B). Thus, mutation of either the MB1 T58 residue or deletion of the Bin1 MBD relieved bin1 inhibition of myc transformation. Bin1 also inhibited E1A-dependent transformation, consistent with the fact that E1A and Myc function similarly in biological assays [G. Evan et al, *Cell*, 69:119–128 (1992); H. Land et al, cited above; H. Ruley, *Nature*, 304:602–606 (1983); and L. Rao et al, *Proc. Natl. Acad. Sci. USA*, 89:7742–7746 (1992)]. However, Bin1 did not affect T antigen-dependent transformation. This result indicated that the inhibition of Myc and E1A was not due to toxicity or nonspecific inhibition of the transformed phenotype. Notably, Bin1ΔMBD significantly inhibited E1A but not Myc. Although the means by which Bin1 and Bin1ΔMBD inhibited E1A was unclear, an important implication of this result was that Bin1 inhibited E1A and Myc by different mechanisms. Supporting the notion that Bin1 was incompatible with Myc or E1A transformation, exogenous Bin1 message accumulated in REF cell populations derived from transformation with T antigen but not with Myc or E1A; in contrast, Bin1ΔMBD message accumulated in REFs transformed by Myc. There is a possibility that a reduced activity of Bin1ΔMBD revealed intrinsic differences in the sensitivity of E1A and Myc to Bin1 inhibition. However, with this caveat, it was concluded that Bin1 physiologically interacted with and inhibited Myc, since deletion of a Bin1 domain sufficient for association in vitro was necessary for its inhibition activity in vivo.

In contrast to the effect of full-length Bin1, but consistent with a dominant inhibitory effect, the murine vector neoCMV-ATG99 specifically augmented focus formation ~2.4-fold when cotransfected with myc and ras. Confirming a dominant inhibitory effect, titration of clone #99 into the REF assay was observed to reverse inhibition of myc and ras by bin1 (data not shown). When taken together with the in vitro biochemical association results, the REF transformation data provided genetic evidence that Bin1 and Myc could interact in vivo. First, mutations in either molecule (T58M in Myc MB1, ΔMBD in Bin1) eliminated bin1 inhibition. Second, a portion of Bin1 encompassing the MBD alone (clone #99) increased myc transforming activity through a dominant inhibitory activity. Finally, since the MBD was sufficient and the Myc boxes were necessary for association in vitro, there was good correlation between the regions involved in protein-protein association and the regions required for biological action. It was therefore concluded that Bin1 inhibited Myc by directly interacting with it in vivo.

Example 8

Rearrangement and loss of expression of the Bin1 gene in liver and breast cancer cells A. Southern Analysis Because Bin1 had been demonstrated to inhibit Myc-dependent cell transformation and tumor cell growth, the following study was performed to determine if the Bin1 gene is mutated in human tumor cells. The initial experiment was to perform Southern analysis of the genomic DNA from a panel of human tumor cell lines including HeLa [cervix, ATCC CCL 2], SK-CO-1 [colon, ATCC HTB 39], HT-29 [colon, ATCC HTB 38], DU145 [prostate, ATCC HTB 41], PC-3 [prostate, ATCC CRL 1435], LNCaP [prostate, ATCC CRL 1740]; T24 [bladder, ATCC HTB4]; MCF7 [breast, ATCC HTB 22]; HepG2 [liver, ATCC HB 8065]; Rh-30 [myosarcoma, E. C. Douglass et al, "A specific chromosomal abnormality in rhabdosarcoma, *Cytogenet. Cell Genet.*, 45:148–155 (1987)]; Raji [lymphoma, ATCC CCL 86]. DNA from WI-38 normal diploid fibroblasts [ATCC CCL 75] was used as a source of normal DNA.

DNAs were isolated by standard methods (Sambrook et al, cited above) and 5 µg per sample was treated with HindIII restriction endonuclease. Restricted DNA was fractionated on a 0.65% agarose gel which was denatured 2×15 minutes in 1.5M NaCl/0.5M NaOH, neutralized 2×30 minutes in 1.5M NaCl/0.5 TrisCl pH 8, and then blotted to a charged nylon membrane (Stratagene, La Jolla Calif.). The blot was crosslinked by UV irradiation and hybridized in a commercial hybridization solution with a random-primed $^{32}$P-labeled Bin1 cDNA probe according to the vendor's instructions (Amersham, Cambridge UK). The blot was washed 1×10 minutes with 2×SSC/0.1% SDS at 20° C. and then 2×10 minutes with 0.2 SSC/0.1% SDS at 65° C. before being exposed to X-ray film (DuPont, Wilmington Del.).

Two bands of >20 kb and 6.5 kb were observed in all the genomic DNAs except for HepG2, a liver carcinoma cell line, where an additional band of ~3.5 kb was seen. Following this observation, a second Southern analysis was performed on a panel of 9 liver carcinoma cell lines, including Huh1, Huh2, HepG2 [ATCC HB8065], Hep3B [ATCC HB8064], Hep43, Hep63, HLF [ATCC CCL 199], NCH2, and NHep40 (provided by Dr. D. Simon, Medical College of Pennsylvania). Conditions were the same as above except that PstI restriction endonuclease was used.

Five bands of 2.5, 1.8, 1.5, 0.95, and 0.75 kb were observed in WI-38 normal DNA. Four of the nine liver tumor DNAs (HepG2, Hep3B, NCH2, and NHep40) exhibited an additional band of 2.9–3.3 kb. These data corroborated the previous results and indicated that Bin1 may be mutated during the development of human hepatocarcinoma.

B. Northern Analysis

Since it could interact with a region of Myc that is mutated in tumors and could inhibit Myc transformation, Bin1 was hypothesized to represent a tumor suppressor gene product. Since a hallmark of tumor suppressors is loss of function (due to genetic or epigenetic causes) in tumor cells, Northern analysis of RNA was performed to test this hypothesis.

RNA was isolated from the initial panel of human tumor cells, including HepG2 liver carcinoma cells, and WI-38 cells. A similar analysis of RNAs isolated from mouse embryo or adult tissues was also performed. Total cytoplasmic RNA was purified by standard methods (Sambrook et al, cited above) and 15 µg was fractionated on a 1% formaldehyde agarose gel and blotted as described [G. C. Prendergast and M. D. Cole, Mol. Cell. Biol., 9:124–134 (1989)]. A commercial Northern blot containing RNA from normal human brain, heart, kidney, lung, liver, skeletal muscle, pancreas, and placenta (Clontech, Palo Alto Calif.) was also analyzed. Using the same procedure and conditions as above, the Northern blots were hybridized with Bin1 cDNA probe [G. Church et al, Proc. Natl. Acad. Sci. USA, 81:1991–1995 (1984)], washed, and exposed to X-ray film.

Ubiquitous expression in normal murine and human cells was observed. In the mouse, RNA levels were highest in embryo, adult brain, and adult muscle but lower levels were seen in all other tissues examined. In embryo and brain, at least two transcripts could be resolved, suggesting alternate splicing or differential usage of initiation or polyadenylation sites in some cells. In human cells, RNA levels were similar in WI-38 normal diploid fibroblasts and tumor cells derived from several different tissues. However, Bin1 message levels were undetectable in HepG2 hepatocarcinoma and MCF7 breast carcinoma cells and were >10-fold reduced in SK-CO-1 colon carcinoma cells.

Further analysis of breast and liver carcinoma cells indicated that Bin1 expression was frequently missing. Bin1 RNA was undetectable in 5/7 breast and 4/7 carcinoma cell lines examined. It was also missing in 3/6 primary breast tumors. The absence did not reflect lack of expression in breast cells, in general, because message was plainly detectable in HBL100, a flat nontumorigenic breast cell line, as well as in RNA isolated from primary breast tissues. Similar deficits were also seen in 3/6 cervix and 1/2 lung carcinoma tumor cell lines, suggesting that loss of Bin1 expression may be common to many carcinomas. These data indicated that loss of expression in tumor cell lines was not a feature of cell line establishment or long-term in vitro culturing.

C. Immunohistochemistry

The data from primary tumors was corroborated by immunohistochemical analysis of breast tissue sections, using the Bin1-specific monoclonal antibody 99D. Tissue sections on cover slips were prepared for staining by fixing 30 min at 4° C. with 4% paraformaldehyde and permeabilizing by treatment 3 min with 0.1% Triton X-100. Endogenous peroxidase was quenched by incubating slips 20 min in 0.3% methanol. Tissue was blocked 20 min with 10% normal goat serum in PBS/0.1% BSA, washed, and incubated 30 min in the same buffer with 1:10 dilution of hybridoma supernatant. The Bin1 staining pattern was identified by incubation 30 min with a goat horseradish peroxidase-conjugated anti-mouse antibody (Jackson ImmunoResearch, West Grove, Pa.) followed by a 5 min incubation with substrate. Before mounting, slides were counterstained by a 1 min incubation with 0.04% acidified solution of the cytoplasmic dye light green. Stained sections were photographed at 500× magnification. Bin1 staining was present in the cell nuclei of morphologically normal ductal epithelia. The pattern observed was consistent with the nuclear localization seen earlier and was specific since incubation of sections with secondary antibody alone produced no staining (data not shown). Consistent with the results from Northern analysis, there was little or no staining of frank carcinoma cells. It was concluded that loss of Bin1 expression occurred frequently in breast carcinoma.

Example 9

Colony Formation Assays

The functional significance of deficits in Bin1 message levels in certain tumor cells (as in Example 8) was suggested by G418-resistant cell colony formation experiments performed in three cell lines available from the American Type Culture Collection (Rockville, Md.) that either contained (HeLa) or lacked (HepG2, MCF7) endogenous Bin1 RNA.

Colony formation assays were performed in the following manner. $3 \times 10^5$ cells in 3 cm dishes were transfected overnight with 2 µg CMV-Bin1 (described in Example 4) or an empty vector, using Lipofectamine (Gibco/BRL). Cells were passaged 48 hr after transfection at a 1:10 ratio into 6 cm dishes containing media with ~0.6 mg/ml G418, which permits selection for the neomycin gene present on each plasmid. Drug-resistant cell colonies were scored by crystal violet staining 2–3 weeks later. At least three trials for each cell line were performed and colonies were scored in triplicate dishes.

Figure 4:
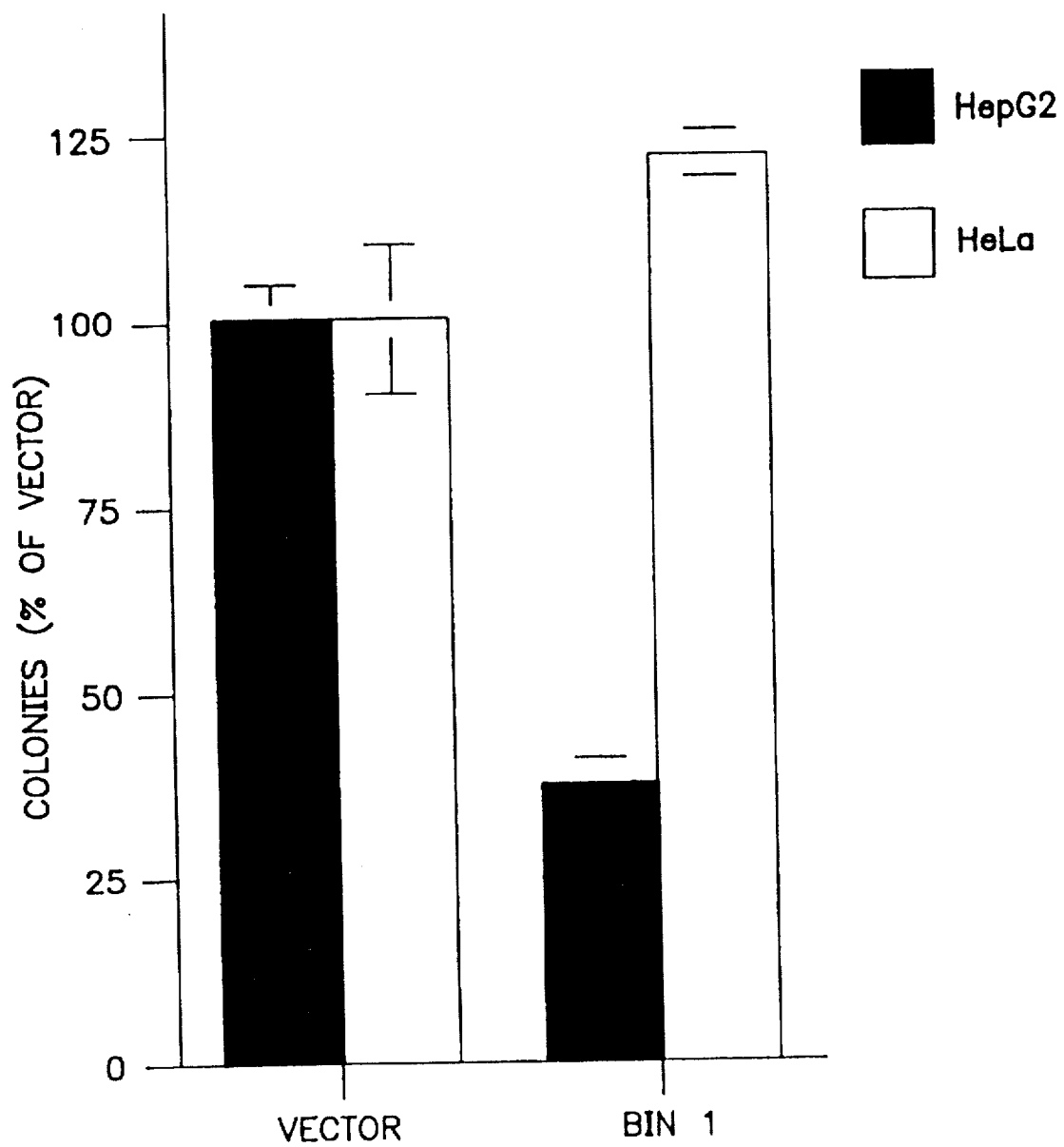
FIG. 4 is a bar chart illustrating that Bin1 vectors selectively inhibit colony formation in HepG2 cells lacking endogenous expression. The data are depicted as the percentage of colonies obtained with empty vector.

HepG2 and MCF7 cells transfected with a Bin1 vector carrying a neomycin-resistance gene exhibited approximately 3-fold fewer colonies relative to cells transfected with empty vector, whereas no significant difference in HeLa colony formation was seen (FIG. 4). This could not be explained by either a general toxic effect or reduced transfection efficiency because the colony formation efficiency of all vectors was similar in HeLa cells. Cell populations derived from pooled colonies which emerged from Bin1-transfected HepG2 cultures showed no evidence of expression, when examined by immunoprecipitation, consistent with an incompatibility with cell growth. From this data, it can be concluded that the RNA deficits seen in carcinoma cells are functionally significant and that Bin1 is capable of exerting a tumor suppressor function.

All documents cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A mammalian Box-dependent myc-interacting polypeptide Bin1, said polypeptide having the amino acid sequence selected from the group consisting of
   (a) murine Bin1, SEQ ID NO:2; and
   (b) human Bin1, SEQ ID NO:4.

2. A polypeptide selected from the group consisting of:
   (a) amino acids 378 to 451 of SEQ ID NO:4; and
   (b) amino acids 270 to 383 of SEQ ID NO: 4.

3. A peptide derived from a mammalian Box-dependent myc-interacting polypeptide Bin1, said polypeptide having the amino acid sequence selected from the group consisting of:
   (a) amino acids 252 to 261 of SEQ ID NO: 4;
   (b) amino acids 190 to 250 of SEQ ID NO: 4;
   (c) amino acids 263 to 397 of SEQ ID NO: 4;
   (d) amino acids 223 to 251 of SEQ ID NO: 4; and
   (e) amino acids 1 to 222 SEQ ID NO: 4.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..399

( x i ) SEQUENCE DESCRIPTION: SEQ ID NO:1:

```
GAG ATC AGA GTG AAC CAT GAG CCA GAG CCG GCC AGT GGG GCC TCA CCC        48
Glu Ile Arg Val Asn His Glu Pro Glu Pro Ala Ser Gly Ala Ser Pro
 1               5                  10                  15

GGG GCT GCC ATC CCC AAG TCC CCA TCT CAG CCA GCA GAG GCC TCC GAG        96
Gly Ala Ala Ile Pro Lys Ser Pro Ser Gln Pro Ala Glu Ala Ser Glu
             20                  25                  30

GTG GTG GGT GGA GCC CAG GAG CCA GGG GAG ACA GCA GCC AGT GAA GCA       144
Val Val Gly Gly Ala Gln Glu Pro Gly Glu Thr Ala Ala Ser Glu Ala
         35                  40                  45

ACC TCC AGC TCT CTT CCG GCT GTG GTG GTG GAG ACC TTC TCC GCA ACT       192
Thr Ser Ser Ser Leu Pro Ala Val Val Val Glu Thr Phe Ser Ala Thr
     50                  55                  60

GTG AAT GGG GCG GTG GAG GGC AGC GCT GGG ACT GGA CGC TTG GAC CTG       240
Val Asn Gly Ala Val Glu Gly Ser Ala Gly Thr Gly Arg Leu Asp Leu
 65                  70                  75                  80

CCC CCG GGA TTC ATG TTC AAG GTT CAA GCC CAG CAT GAT TAC ACG GCC       288
Pro Pro Gly Phe Met Phe Lys Val Gln Ala Gln His Asp Tyr Thr Ala
                 85                  90                  95

ACT GAC ACT GAT GAG CTG CAA CTC AAA GCT GGC GAT GTG GTG TTG GTG       336
Thr Asp Thr Asp Glu Leu Gln Leu Lys Ala Gly Asp Val Val Leu Val
             100                 105                 110

ATT CCT TTC CAG AAC CCA GAG GAG CAG GAT GAA GGC TGG CTC ATG GGT       384
Ile Pro Phe Gln Asn Pro Glu Glu Gln Asp Glu Gly Trp Leu Met Gly
         115                 120                 125

GTG AAG GAG AGC GAC TGA                                               402
Val Lys Glu Ser Asp
     130
```

( 2 ) INFORMATION FOR SEQ ID NO:2:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Glu Ile Arg Val Asn His Glu Pro Glu Pro Ala Ser Gly Ala Ser Pro
 1               5                  10                  15

Gly Ala Ala Ile Pro Lys Ser Pro Ser Gln Pro Ala Glu Ala Ser Glu
             20                  25                  30

Val Val Gly Gly Ala Gln Glu Pro Gly Glu Thr Ala Ala Ser Glu Ala
         35                  40                  45
```

```
Thr  Ser  Ser  Ser  Leu  Pro  Ala  Val  Val  Glu  Thr  Phe  Ser  Ala  Thr
     50                  55                  60

Val  Asn  Gly  Ala  Val  Glu  Gly  Ser  Ala  Gly  Thr  Gly  Arg  Leu  Asp  Leu
65                       70                       75                        80

Pro  Pro  Gly  Phe  Met  Phe  Lys  Val  Gln  Ala  Gln  His  Asp  Tyr  Thr  Ala
               85                      90                      95

Thr  Asp  Thr  Asp  Glu  Leu  Gln  Leu  Lys  Ala  Gly  Asp  Val  Val  Leu  Val
          100                      105                      110

Ile  Pro  Phe  Gln  Asn  Pro  Glu  Glu  Gln  Asp  Glu  Gly  Trp  Leu  Met  Gly
          115                      120                      125

Val  Lys  Glu  Ser  Asp
          130
```

(2) INFORMATION FOR SEQ ID NO:3:

(i) SEQUENCE CHARACTERISTICS:
        (A) LENGTH: 1925 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 60..1412

(xi) SEQUENCE DESCRIPTION: SEQ ID NO:3:

```
GAATTCCGTG CTGGTTGAGC TTGCTCATCT CCTTGTGGAA GTTTTCCTCC AGGCCCGCG                    59

ATG  CTC  TGG  AAC  GTG  GTG  ACG  GCG  GGA  AAG  ATC  GCC  AGC  AAC  GTG  CAG    107
Met  Leu  Trp  Asn  Val  Val  Thr  Ala  Gly  Lys  Ile  Ala  Ser  Asn  Val  Gln
1                   5                        10                       15

AAG  AAG  CTC  ACC  CGC  GCG  CAG  GAG  AAG  GTT  CTC  CAG  AAG  CTG  GGG  AAG    155
Lys  Lys  Leu  Thr  Arg  Ala  Gln  Glu  Lys  Val  Leu  Gln  Lys  Leu  Gly  Lys
               20                       25                       30

GCA  GAT  GAG  ACC  AAG  GAT  GAG  CAG  TTT  GAG  CAG  TGC  GTC  CAG  AAT  TTC    203
Ala  Asp  Glu  Thr  Lys  Asp  Glu  Gln  Phe  Glu  Gln  Cys  Val  Gln  Asn  Phe
          35                       40                       45

AAC  AAG  CAG  CTG  ACG  GAG  GGC  ACC  CGG  CTG  CAG  AAG  GAT  CTC  CGG  ACC    251
Asn  Lys  Gln  Leu  Thr  Glu  Gly  Thr  Arg  Leu  Gln  Lys  Asp  Leu  Arg  Thr
     50                       55                       60

TAC  CTG  GCC  TCC  GTC  AAA  GCC  ATG  CAC  GAG  GCT  TCC  AAG  AAG  CTG  AAT    299
Tyr  Leu  Ala  Ser  Val  Lys  Ala  Met  His  Glu  Ala  Ser  Lys  Lys  Leu  Asn
65                       70                       75                       80

GAG  TGT  CTG  CAG  GAG  GTG  TAT  GAG  CCC  GAT  TGG  CCC  GGC  AGG  GAT  GAG    347
Glu  Cys  Leu  Gln  Glu  Val  Tyr  Glu  Pro  Asp  Trp  Pro  Gly  Arg  Asp  Glu
               85                       90                       95

GCA  AAC  AAG  ATC  GCA  GAG  AAC  AAC  GAC  CTG  CTG  TGG  ATG  GAT  TAC  CAC    395
Ala  Asn  Lys  Ile  Ala  Glu  Asn  Asn  Asp  Leu  Leu  Trp  Met  Asp  Tyr  His
          100                      105                      110

CAG  AAG  CTG  GTG  GAC  CAG  GCG  CTG  CTG  ACC  ATG  GAC  ACG  TAC  CTG  GGC    443
Gln  Lys  Leu  Val  Asp  Gln  Ala  Leu  Leu  Thr  Met  Asp  Thr  Tyr  Leu  Gly
          115                      120                      125

CAG  TTC  CCC  GAC  ATC  AAG  TCA  CGC  ATT  GCC  AAG  CGG  GGG  CGC  AAG  CTG    491
Gln  Phe  Pro  Asp  Ile  Lys  Ser  Arg  Ile  Ala  Lys  Arg  Gly  Arg  Lys  Leu
     130                      135                      140

GTG  GAC  TAC  GAC  AGT  GCC  CGG  CAC  CAC  TAC  GAG  TCC  CTT  CAA  ACT  GCC    539
Val  Asp  Tyr  Asp  Ser  Ala  Arg  His  His  Tyr  Glu  Ser  Leu  Gln  Thr  Ala
145                      150                      155                      160

AAA  AAG  AAG  GAT  GAA  GCC  AAA  ATT  GCC  AAG  GCC  GAG  GAG  GAG  CTC  ATC    587
Lys  Lys  Lys  Asp  Glu  Ala  Lys  Ile  Ala  Lys  Ala  Glu  Glu  Glu  Leu  Ile
```

-continued

| | | | | | | | | | | | | | | | | |
|---|---|---|---|---|---|---|---|---|---|---|---|---|---|---|---|---|
| | | | 165 | | | | | 170 | | | | | 175 | | | |
| AAA | GCC | CAG | AAG | GTG | TTT | GAG | GAG | ATG | AAT | GTG | GAT | CTG | CAG | GAG | GAG | 635 |
| Lys | Ala | Gln | Lys | Val | Phe | Glu | Glu | Met | Asn | Val | Asp | Leu | Gln | Glu | Glu | |
| | | | 180 | | | | | 185 | | | | | 190 | | | |
| CTG | CCG | TCC | CTG | TGG | AAC | AGC | CGC | GTA | GGT | TTC | TAC | GTC | AAC | ACG | TTC | 683 |
| Leu | Pro | Ser | Leu | Trp | Asn | Ser | Arg | Val | Gly | Phe | Tyr | Val | Asn | Thr | Phe | |
| | | 195 | | | | | 200 | | | | | 205 | | | | |
| CAG | AGC | ATC | GCG | GGC | CTG | GAG | GAA | AAC | TTC | CAC | AAG | GAG | ATG | AGC | AAG | 731 |
| Gln | Ser | Ile | Ala | Gly | Leu | Glu | Glu | Asn | Phe | His | Lys | Glu | Met | Ser | Lys | |
| | | 210 | | | | | 215 | | | | | 220 | | | | |
| CTC | AAC | CAG | AAC | CTC | AAT | GAT | GTG | CTG | GTC | GGC | CTG | GAG | AAG | CAA | CAC | 779 |
| Leu | Asn | Gln | Asn | Leu | Asn | Asp | Val | Leu | Val | Gly | Leu | Glu | Lys | Gln | His | |
| 225 | | | | | 230 | | | | | 235 | | | | | 240 | |
| GGG | AGC | AAC | ACC | TTC | ACG | GTC | AAG | GCC | CAG | CCC | AGA | AAG | AAA | AGT | AAA | 827 |
| Gly | Ser | Asn | Thr | Phe | Thr | Val | Lys | Ala | Gln | Pro | Arg | Lys | Lys | Ser | Lys | |
| | | | | 245 | | | | | 250 | | | | | 255 | | |
| CTG | TTT | TCG | CGG | CTG | CGC | AGA | AAG | AAG | AAC | AGT | GAC | AAC | GCG | CCT | GCA | 875 |
| Leu | Phe | Ser | Arg | Leu | Arg | Arg | Lys | Lys | Asn | Ser | Asp | Asn | Ala | Pro | Ala | |
| | | | 260 | | | | | 265 | | | | | 270 | | | |
| AAA | GGG | AAC | AAG | AGC | CCT | TCG | CCT | CCA | GAT | GGC | TCC | CCT | GCC | GCC | ACC | 923 |
| Lys | Gly | Asn | Lys | Ser | Pro | Ser | Pro | Pro | Asp | Gly | Ser | Pro | Ala | Ala | Thr | |
| | | 275 | | | | | 280 | | | | | 285 | | | | |
| CCC | GAG | ATC | AGA | GTC | AAC | CAC | GAG | CCA | GAG | CCG | GCC | GGC | GGG | GCC | ACG | 971 |
| Pro | Glu | Ile | Arg | Val | Asn | His | Glu | Pro | Glu | Pro | Ala | Gly | Gly | Ala | Thr | |
| | 290 | | | | | 295 | | | | | 300 | | | | | |
| CCC | GGG | GCC | ACC | CTC | CCC | AAG | TCC | CCA | TCT | CAG | CCA | GCA | GAG | GCC | TCG | 1019 |
| Pro | Gly | Ala | Thr | Leu | Pro | Lys | Ser | Pro | Ser | Gln | Pro | Ala | Glu | Ala | Ser | |
| 305 | | | | | 310 | | | | | 315 | | | | | 320 | |
| GAG | GTG | GCG | GGT | GGG | ACC | CAA | CCT | GCG | GCT | GGA | GCC | CAG | GAG | CCA | GGG | 1067 |
| Glu | Val | Ala | Gly | Gly | Thr | Gln | Pro | Ala | Ala | Gly | Ala | Gln | Glu | Pro | Gly | |
| | | | | 325 | | | | | 330 | | | | | 335 | | |
| GAG | ACG | GCG | GCA | AGT | GAA | GCA | GCC | TCC | AGC | TCT | CTT | CCT | GCT | GTC | GTG | 1115 |
| Glu | Thr | Ala | Ala | Ser | Glu | Ala | Ala | Ser | Ser | Ser | Leu | Pro | Ala | Val | Val | |
| | | | 340 | | | | | 345 | | | | | 350 | | | |
| GTG | GAG | ACC | TTC | CCA | GCA | ACT | GTG | AAT | GGC | ACC | GTG | GAG | GGC | GGC | AGT | 1163 |
| Val | Glu | Thr | Phe | Pro | Ala | Thr | Val | Asn | Gly | Thr | Val | Glu | Gly | Gly | Ser | |
| | | 355 | | | | | 360 | | | | | 365 | | | | |
| GGG | GCC | GGG | CGC | TTG | GAC | CTG | CCC | CCA | GGT | TTC | ATG | TTC | AAG | GTA | CAG | 1211 |
| Gly | Ala | Gly | Arg | Leu | Asp | Leu | Pro | Pro | Gly | Phe | Met | Phe | Lys | Val | Gln | |
| | 370 | | | | | 375 | | | | | 380 | | | | | |
| GCC | CAG | CAC | GAC | TAC | ACG | GCC | ACT | GAC | ACA | GAC | GAG | CTG | CAG | CTC | AAG | 1259 |
| Ala | Gln | His | Asp | Tyr | Thr | Ala | Thr | Asp | Thr | Asp | Glu | Leu | Gln | Leu | Lys | |
| 385 | | | | | 390 | | | | | 395 | | | | | 400 | |
| GCT | GGT | GAT | GTG | GTG | CTG | GTG | ATC | CCC | TTC | CAG | AAC | CCT | GAA | GAG | CAG | 1307 |
| Ala | Gly | Asp | Val | Val | Leu | Val | Ile | Pro | Phe | Gln | Asn | Pro | Glu | Glu | Gln | |
| | | | | 405 | | | | | 410 | | | | | 415 | | |
| GAT | GAA | GGC | TGG | CTC | ATG | GGC | GTG | AAG | GAG | AGC | GAC | TGG | AAC | CAG | CAC | 1355 |
| Asp | Glu | Gly | Trp | Leu | Met | Gly | Val | Lys | Glu | Ser | Asp | Trp | Asn | Gln | His | |
| | | | 420 | | | | | 425 | | | | | 430 | | | |
| AAG | AAG | CTG | GAG | AAG | TGC | CGT | GGC | GTC | TTC | CCC | GAG | AAC | TTC | ACT | GAG | 1403 |
| Lys | Lys | Leu | Glu | Lys | Cys | Arg | Gly | Val | Phe | Pro | Glu | Asn | Phe | Thr | Glu | |
| | | 435 | | | | | 440 | | | | | 445 | | | | |
| AGG | GTC | CCA | TGACGGCGGG | GCCCAGGCAG | CCTCCGGGCG | TGTGAAGAAC | | | | | | | | | | 1452 |
| Arg | Val | Pro | | | | | | | | | | | | | | |
| | | 450 | | | | | | | | | | | | | | |

| | |
|---|---|
| ACCTCCTCCC GAAAAATGTG TGGTTCTTTT TTTTGTTTTG TTTTCGTTTT TCATCTTTTG | 1512 |
| AAGAGCAAAG GGAAATCAAG AGGAGACCCC CAGGCAGAGG GGCGTTCTCC CAAAGTTTAG | 1572 |
| GTCGTTTTCC AAAAGAGCCGC GTCCCGGCAA GTCCGGCGGA ATTCACCAGT GTTCCTGAAG | 1632 |

```
CTGCTGTGTC CTCTAGTTGA GTTTCTGGCG CCCCTGCCTG TGCCCGCATG TGTGCCTGGC    1692

CGCAGGGCGG GGCTGGGGGC TGCCGAGCCA CCATACTTAA CTGAAGCTTC GGCCGCACCA    1752

CCCGGGGAAG GGTCCTCTTT TCCTGGCAGC TGCTGTGGGT GGGGCCCAGA CACCAGCCTA    1812

GCCTGCTCTG CCCCGCAGAC GGTCTGTGTG CTGTTTGAAA ATAAATCTTA GTGTTCAAAA    1872

CAAAATGAAA CAAAAAAAAA AATGATAAAA ACTCTCAAAA AAACAAGGAA TTC           1925
```

( 2 ) INFORMATION FOR SEQ ID NO:4:

( i ) SEQUENCE CHARACTERISTICS:
( A ) LENGTH: 451 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met  Leu  Trp  Asn  Val  Val  Thr  Ala  Gly  Lys  Ile  Ala  Ser  Asn  Val  Gln
 1              5                        10                       15

Lys  Lys  Leu  Thr  Arg  Ala  Gln  Glu  Lys  Val  Leu  Gln  Lys  Leu  Gly  Lys
              20                        25                       30

Ala  Asp  Glu  Thr  Lys  Asp  Glu  Gln  Phe  Glu  Gln  Cys  Val  Gln  Asn  Phe
              35                        40                       45

Asn  Lys  Gln  Leu  Thr  Glu  Gly  Thr  Arg  Leu  Gln  Lys  Asp  Leu  Arg  Thr
         50                   55                       60

Tyr  Leu  Ala  Ser  Val  Lys  Ala  Met  His  Glu  Ala  Ser  Lys  Lys  Leu  Asn
 65                   70                       75                            80

Glu  Cys  Leu  Gln  Glu  Val  Tyr  Glu  Pro  Asp  Trp  Pro  Gly  Arg  Asp  Glu
                   85                        90                       95

Ala  Asn  Lys  Ile  Ala  Glu  Asn  Asn  Asp  Leu  Leu  Trp  Met  Asp  Tyr  His
                  100                       105                      110

Gln  Lys  Leu  Val  Asp  Gln  Ala  Leu  Leu  Thr  Met  Asp  Thr  Tyr  Leu  Gly
              115                       120                      125

Gln  Phe  Pro  Asp  Ile  Lys  Ser  Arg  Ile  Ala  Lys  Arg  Gly  Arg  Lys  Leu
     130                       135                      140

Val  Asp  Tyr  Asp  Ser  Ala  Arg  His  His  Tyr  Glu  Ser  Leu  Gln  Thr  Ala
145                       150                      155                      160

Lys  Lys  Lys  Asp  Glu  Ala  Lys  Ile  Ala  Lys  Ala  Glu  Glu  Glu  Leu  Ile
                  165                       170                      175

Lys  Ala  Gln  Lys  Val  Phe  Glu  Glu  Met  Asn  Val  Asp  Leu  Gln  Glu  Glu
              180                       185                      190

Leu  Pro  Ser  Leu  Trp  Asn  Ser  Arg  Val  Gly  Phe  Tyr  Val  Asn  Thr  Phe
         195                       200                      205

Gln  Ser  Ile  Ala  Gly  Leu  Glu  Glu  Asn  Phe  His  Lys  Glu  Met  Ser  Lys
210                       215                      220

Leu  Asn  Gln  Asn  Leu  Asn  Asp  Val  Leu  Val  Gly  Leu  Glu  Lys  Gln  His
225                       230                      235                      240

Gly  Ser  Asn  Thr  Phe  Thr  Val  Lys  Ala  Gln  Pro  Arg  Lys  Lys  Ser  Lys
                  245                       250                      255

Leu  Phe  Ser  Arg  Leu  Arg  Arg  Lys  Lys  Asn  Ser  Asp  Asn  Ala  Pro  Ala
              260                       265                      270

Lys  Gly  Asn  Lys  Ser  Pro  Ser  Pro  Asp  Gly  Ser  Pro  Ala  Ala  Thr
         275                       280                      285

Pro  Glu  Ile  Arg  Val  Asn  His  Glu  Pro  Glu  Pro  Ala  Gly  Gly  Ala  Thr
     290                       295                      300

Pro  Gly  Ala  Thr  Leu  Pro  Lys  Ser  Pro  Ser  Gln  Pro  Ala  Glu  Ala  Ser
```

|     |     |     |     |     |     |     |     |     |     |     |     |     |     |     |
|-----|-----|-----|-----|-----|-----|-----|-----|-----|-----|-----|-----|-----|-----|-----|
| 305 |     |     |     |     | 310 |     |     |     |     | 315 |     |     |     | 320 |
| Glu | Val | Ala | Gly | Gly | Thr | Gln | Pro | Ala | Ala | Gly | Ala | Gln | Glu | Pro | Gly |
|     |     |     |     | 325 |     |     |     | 330 |     |     |     |     | 335 |
| Glu | Thr | Ala | Ala | Ser | Glu | Ala | Ala | Ser | Ser | Ser | Leu | Pro | Ala | Val | Val |
|     |     |     | 340 |     |     |     | 345 |     |     |     |     | 350 |
| Val | Glu | Thr | Phe | Pro | Ala | Thr | Val | Asn | Gly | Thr | Val | Glu | Gly | Gly | Ser |
|     |     | 355 |     |     |     | 360 |     |     |     | 365 |
| Gly | Ala | Gly | Arg | Leu | Asp | Leu | Pro | Pro | Gly | Phe | Met | Phe | Lys | Val | Gln |
|     | 370 |     |     |     | 375 |     |     |     | 380 |
| Ala | Gln | His | Asp | Tyr | Thr | Ala | Thr | Asp | Thr | Asp | Glu | Leu | Gln | Leu | Lys |
| 385 |     |     |     | 390 |     |     |     | 395 |     |     |     |     | 400 |
| Ala | Gly | Asp | Val | Val | Leu | Val | Ile | Pro | Phe | Gln | Asn | Pro | Glu | Glu | Gln |
|     |     |     | 405 |     |     |     | 410 |     |     |     | 415 |
| Asp | Glu | Gly | Trp | Leu | Met | Gly | Val | Lys | Glu | Ser | Asp | Trp | Asn | Gln | His |
|     |     | 420 |     |     |     | 425 |     |     |     | 430 |
| Lys | Lys | Leu | Glu | Lys | Cys | Arg | Gly | Val | Phe | Pro | Glu | Asn | Phe | Thr | Glu |
|     | 435 |     |     |     | 440 |     |     |     | 445 |
| Arg | Val | Pro |
| 450 |

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:5:

| Glu | Asp | Ile | Trp | Lys | Lys | Phe | Glu | Leu | Leu | Pro | Thr | Pro | Pro | Leu | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |

( 2 ) INFORMATION FOR SEQ ID NO:6:

( i ) SEQUENCE CHARACTERISTICS:
        ( A ) LENGTH: 14985 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: unsure
        ( B ) LOCATION: 1332
        ( D ) OTHER INFORMATION: /note= "unsequenced segment"

( i x ) FEATURE:
        ( A ) NAME/KEY: unsure
        ( B ) LOCATION: 3225
        ( D ) OTHER INFORMATION: /note= "unsequenced segment"

( i x ) FEATURE:
        ( A ) NAME/KEY: unsure
        ( B ) LOCATION: 7209
        ( D ) OTHER INFORMATION: /note= "unsequenced segment"

( i x ) FEATURE:
        ( A ) NAME/KEY: unsure
        ( B ) LOCATION: 11097
        ( D ) OTHER INFORMATION: /note= "unsequenced segment"

( i x ) FEATURE:
        ( A ) NAME/KEY: exon
        ( B ) LOCATION: 1..324
        ( D ) OTHER INFORMATION: /note= "Exon 1"

( i x ) FEATURE:
    ( A ) NAME/KEY: exon
    ( B ) LOCATION: 325..1618
    ( D ) OTHER INFORMATION: /note= "Exon 2"

( i x ) FEATURE:
    ( A ) NAME/KEY: exon
    ( B ) LOCATION: 1619..3174
    ( D ) OTHER INFORMATION: /note= "Exon 3"

( i x ) FEATURE:
    ( A ) NAME/KEY: exon
    ( B ) LOCATION: 3175..4365
    ( D ) OTHER INFORMATION: /note= "Exon 4"

( i x ) FEATURE:
    ( A ) NAME/KEY: exon
    ( B ) LOCATION: 4441..11518
    ( D ) OTHER INFORMATION: /note= "Exon 5"

( i x ) FEATURE:
    ( A ) NAME/KEY: exon
    ( B ) LOCATION: 11519..11850
    ( D ) OTHER INFORMATION: /note= "Exon 6"

( i x ) FEATURE:
    ( A ) NAME/KEY: exon
    ( B ) LOCATION: 11851..12240
    ( D ) OTHER INFORMATION: /note= "Exon 7"

( i x ) FEATURE:
    ( A ) NAME/KEY: exon
    ( B ) LOCATION: 12241..14129
    ( D ) OTHER INFORMATION: /note= "Exon 8"

( i x ) FEATURE:
    ( A ) NAME/KEY: exon
    ( B ) LOCATION: 14130..14985
    ( D ) OTHER INFORMATION: /note= "Exon 9"

( x i ) SEQUENCE DESCRIPTION: SEQ ID NO:6:

```
TCGATCTAGC AGGATGAGCT GCCGTCCCTG TGGAACAGGT GAGGCCCGGC ACGGTGCCCA      60
GCCTGCGTGG GGCAGTGTCC AGTCTGCGTG CTGCAGTGCC CAGTCTGCGT GCTGTGGTGC     120
CCAGCCTGCG TGCTGCGGTG TCCAGTCTGC GTGCTGCGGT GCCCAGCCTG TGTGCTGCAG     180
TGTCCAGCCT GAGTGCTGCG GTGCCTGGGC CCTCTCTGGT TTGTGCCTCT GATGAGCGTG     240
TGTGGTCGCT CGTGGGTGGG TATTTCTGAG TTGCTGTCCT GACCTGCCTG TTCACCTGGC     300
CCCCATCCTT CCGCCCTTCT GTAGCCGCGT AGGTTTCTAC GTCAACACGT TCCAGAGCAT     360
CGCGGGCCTG GAGGAAAACT TCCACAAGGA GATGAGCAAG GTAGGCCATG GGACCCCTC      420
TGAGGGGCCA CACCCCACCC TGGCCGAGGG TCAGAGTCAG AATCGTGGGA GGGGCAGCCT     480
GAACTCCTCC TTCCCTGCCA GGTTCAGCAC ACACCGGTGA CCACAGGGCT CCCTCCCGGC     540
CCTGGTGGAA CAGCCCCCTT CAGGAGTGCC TGGGCCCAG GAAGGGCACC AGGGCATGCT      600
GGGGAGGCTT TGAGAGTGTC CTGGGTCCTT GCCTGGGTAG ACCACCTGAG AATGTAGACC     660
AGGCCCTCTC AAACTGTGAA TGTGTTCTCT AGCAACCTTG GCCAGGGAG TGCAGTGTTA      720
GACAATGGTG GCAGTTTCTC AATTTGTAGG AAAAAATTAC TAGCATTTTC TCAATTTTAA     780
TTTTTCTCCC ATGCTTTGA GACATTTAAA TAGGCCTGTT TCGTCTGCGT GAATCCACTG      840
TGCGACAGGG TCTGGTCTGA TTAGCGTACC TTTCTCTCTT GTGTTATTTT CATTTTAACC     900
TATCTGGCAA CTAAAACGCA AAGCTGTTGA ACTTTGCAGT GGAGAGACC CAGGGCTGGC      960
ACCCCCGCCC CCAGTGGTGG GTCTGACTTT GTCTCTTGGG CCCAGATGGA TGAAGTGATG    1020
ATGGTGGATT CCAGGCCCAG GGTCGGAGGA GGAAAAGCAG CTTGGGGCCT CCCCTGACTC    1080
ACACTTCTAA GTACGGTTTC CTGCCTTTTA GACTTTCTCT TTCCTTCTTA ACTTTTCCTT    1140
```

```
TTTCCCTTCG AAGATTGGAG ACAACTTACG AAAAGTTTAA AAAATAGAGA AAGGTGTTTC     1200
AGAGAAGGAA CATTTATATA AAATTAGTCT GTAAAATAT  ATGCCACAGA ACATAGTTGT     1260
TTATAAATAG GATGAAGATT CGGCCTGAGC TCCTAGTGGC CAAATCAAAG AAANGAATAT     1320
CTCAGTAATG ANGGNGTTNA TAATGGGGCA TTTTAGGATA TCCCTAATAA GTAGGGAGGG     1380
GAAAAGATGG TTCCAAGAGA CAGCAGGCAT TAGNGATATA GCCCANTTGC CCGGTTTTNG     1440
NNGCCCCCTN GGTTTTTGGG GGGNTTGGTG TGCNAGTTCC TTGCTCTCAC AGATGGGGAA     1500
AGAGGAGCTT GTTCCTGGCA GGGGCTGGGG GTGGTGGGGA GAAGCAGAGG TGTTTGGGGA     1560
AGGTGGGGCC GTTTGGTGGC CTTGGAGGCC CCCCACCTCC TCACTGTCTC TCCTGCAGCT     1620
CAACCAGAAC CTCAATGATG TGCTGGTCGG CCTGGAGAAG CAACACGGGA GCAACACCTT     1680
CACGGTCAAG GCCCAGCCCA GGTGCGTGCG GGAGAGCCC  TGGCGCCCCT GACTGTGTGC     1740
ACGGCAGGGG CAGGGCTCCT TCCTGTGACC CTGTTGGTGC CCTCCCTGG  TCCCCCATGG     1800
GTTTGGCCTT GGGGGTCTAG GGACCTTCCT GTCTTGGCCT CTCTGTGCTC AGGGAGGCAG     1860
GTGAGGGCAG GTCTCTGTCT CGAATGTCCC TGCCCCTCTG GCTGTGTTCG TCGAGGAAGG     1920
AGCACTCTGG GGAGTCCGCG GGTACCCTGA GCCGGCTGAC CCCCTCATTG TGGAGCACGA     1980
GCATCCAGGG TTGGGGTGGG CAGCCTGCTC AGCTTTGGGG ACTGGGGGGT GTGAACAGGA     2040
CTGAAAGACT CCGGGGTGTG CAGTCCTCTC AGAGCAGGGA GATAGCACCG CCCTTCCTCT     2100
CCTGCTNGTG GNAAAAGATC ATGTCCCTGG ATGGCAGCAT TGTGCTCAAC CACANGAGCA     2160
TCCTCTTCCT GTCCTCAGCC TCAGCCCCTC CGGGAATCCC AGCTGCAAGG AGGCCTCTGT     2220
TTCCTGAGGG GAAACCATGA GGGAGGAGGG AAATGCCTTG CTTTCCTGGC TGTGGATCAG     2280
AGGAAGCAGC GAGCCTGGGA CTTCCCCTCC CTTNTGGCCA TGTGTGCATG TGTGTGTGTG     2340
AGGGGGACTG TGTGTGACAG GTGTAAGTGT GTGCATACCC ACACACATAT CACAGCAGAA     2400
CGCAGAGAAC ACCGATGGAC TCTGTAAAAC AGGGCGACTG TCTGCTTCTT GGGGTATTGC     2460
CTGGGATGAT GAGGGTATCG GGTGGTGGTG ATTGCCCCCT CCTTCCCTGA ACATAAAATA     2520
GTTGTGGCTG AGAGAGGGGC CATGGTGACC TGAGGCTGGG AGTGGGGAGG TTAGGACGGT     2580
GGCGTTGTGG TGGTGGTTGG GGGGGTGGGT AGGGGGGTGG GGGTTGGGAT AAAGCCAAAA     2640
GGTGAATTCA AGGTCGGGCA GGGAGGGACA GCTGCCTGGC CTGTAGGCAC AGGTGGGAAC     2700
ANTGGGATGG ATCAGCAGGG GGTAAGTGGG GCCGTCCTGG CCAGAACCAT GGCTCCCCTC     2760
AGGAAGGAGG TGGAGGGAAG AGAGAGGGGC AGTAGAGGCC CAGGAGTCTC CCTTCCAGCA     2820
GAGAGGCCTC TTGTGCACTN TGTGCTCGCC TGGGGGCCTT TTCTGGCACT NTGGGCACAC     2880
CTGGAGCTCC TGGGGACTGG GACCACAGGC AGGGTGACTA TCCACTGCCC CGAGCCTCCT     2940
GCCCCTCACC AGGCCCTGTT AGCATCACCT CGGGCACCTG GCCACAGCAG GGGCCAGTCA     3000
GGGCACCCCG GGATAGCACG CCCAGGCCCT GTGCAAGGCC TCTGGCACTT AGGAGAGGCT     3060
TTTGCCCCTT TGTCCTCTGA GCAGAAGGGT TGGCAAAGAG GGAAGGGGAC AGGCCAGTTC     3120
TGCACCTGGC CTTTCTCCAG AATGAAGGCC TCCACCTCCC GTCCGTCCCC ACAGAAAGAA     3180
AAGTAAACTG TTTTCGCGGC TGCGCAGAAA GAAGAACAGG TACCNAGGAT GGTGCCCCGG     3240
GGCCAACCCA GGGCAATTT  AAGCAAATGG AGGAAGGNGG GNTGGGGAAA GGAGGCNTGG     3300
GGGAGGGCCA GGGAGGGTGA NAATGCAGCA AATGTGGGGG TTTTTGTTT  TTTAAAACAA     3360
ATTGTATGTG TATACCATAT ACTTATACAT ATATTCTTTA AGGAGAATAC ATTCCCATAA     3420
AACACAAATT CCAGAAGGAA AGATGGTGTC AGCGACATCT CTTACGNTGT TCCACTGTTT     3480
GCCCTCAGGT GANTCGGTCA CTGGTTCCTG CTGGATGNTT GTAGATGTGC ACTGTCCAGC     3540
```

-continued

| | | | | | |
|---|---|---|---|---|---|
|ACAGGAGCCA|GTTACCCCAT|GGGGCTATTG|AGCACTTGAA|ACTGGCCAGT|GTGACCGGGC|3600|
|AGCGGAACTT|TTCATTTGAA|TTACACATAA|ATTTCATTGC|TTTGAGTTTG|CATTGCCGCC|3660|
|TGTGGCTAGT|GGCAACCGTA|CTGGGCAGCA|CTTTTCTAGG|CGTCTCTGTG|CAGGTTCTGG|3720|
|TAGAGAATTT|TCTCCCTGCA|CCTTCGCCCC|TGTGCCTGGG|GTGCACAGCA|TCACACCACC|3780|
|TCCGCCTTGG|GTTCTGGCAC|TGAACGCCAT|GGCTCAGGAC|CTGTCCCCTC|CATCGCCAGC|3840|
|TGCCCACTCC|TCTGTGATGA|GGACGCCTCT|CTTAGTTTGT|CCAGGCCCTG|CTTGTGGCCT|3900|
|CCAGCAGCCG|AGAGGACAGG|AGAGCCCAAG|GTCTAGAGAC|ATGTACCAGG|GTGCTGTGAT|3960|
|GGACAGGCAG|GGAGGGCAGC|AGGCTGGGGA|GCAGACCCCA|GAACAGAGGG|GCTGCTGCGT|4020|
|GTGGTGTGGG|AGACTCACTG|TGCCTCTAGG|ATGTCTGGCT|TTCTCCTGCT|GTGGATCTTG|4080|
|GGCTGTCAGC|ATGGGCCCTG|GTGGACCCCA|TGGAGCCTGT|GGGGTGGTTG|GTCTGGTCTC|4140|
|TGCGACAGAT|GGTTCCAAGG|GACCTGCCTG|CACTCCTGGG|GACCATAGAC|CTCCAGCCTG|4200|
|GAGTCCCACC|TTGTGCTGTT|CCTGTTTCTG|AGGCAGGCTT|CCCACTTCCA|GCCCCCAAG|4260|
|CCCAGGTCCC|TTGGCTCCCC|CCACCCTCCT|GCTCTCTCTC|ACATACACAC|ACACACACAC|4320|
|ACACAGTTTC|ACACCTCCAT|ATGCACACAC|CTCTTCACAC|AGACGTCAAT|ACATTTGCCC|4380|
|CTCCGTCTCC|TGTGCCTTGG|CCCCCCAACA|CTGGGCTCCC|TTTCTTGTCC|TCCCCACAG|4440|
|TGACAACGCG|CCTGCAAAAG|GGAACAAGAA|CCCTTCCGCC|TCCAGATGGC|TCCCCTGCCG|4500|
|CCACCCCCGA|GATCAGAGTC|AACCACGACC|AGAGCCGGCC|GGCGGGGCCA|CGCCCGGGGC|4560|
|CACCCTCCCC|AAGTCCCCAT|CTCAGGTAGG|GAGNGAAGTT|TTGGTAGAAG|GTCCAAGCC|4620|
|NTCCATCNAT|NTCGTCNGGG|ATNGGCTGTT|GTCCTCCATC|CTCCCACTCC|CTGTCCCCTT|4680|
|TCTGGCCTGG|GCAGCTATGG|ACCCGATGCT|TTGCCCAGTG|GGGGTTGGGC|CTGGACCTGG|4740|
|GTGTCCTTTC|CCCCATCCAG|CTGGCATGCT|TCCGGGAGGC|ATCTGTGACT|TGCTCGTTCC|4800|
|TCCCCAGCCC|CCACCCCAC|TGCAGCGCCC|TCCCCTTCCC|TCTCCNTGGT|GTTTTGTGAT|4860|
|GNTNGANTCT|TTNTCCATNT|TNTTTTCCTC|CCTAGCAGAG|GGTATGGGCC|CTCAGCCCAC|4920|
|AGAGCATCCA|GATNTCCAGA|GTGGGCTGCC|TGTCCCTNTT|NNTGGCCTCT|CTCTTTTAAA|4980|
|GGGGCCTGAG|GGAGGAGCCC|AAGCCAGGTG|GCCATGCAGG|ACCTTTAAAG|GGACAGAGAG|5040|
|AGGAAGGGGT|CAGAGGAGGG|TGTGGGGTGG|CTAAGGGGGC|AGGTCNTGGG|NTTGTGGANT|5100|
|GTCCTTGTGT|CCACCCCGCC|TGCCCCAGC|GGGCCCTCCA|GGTGTANGCA|GGNCCCTAGG|5160|
|TGCTGGCTGG|CCAGGNGGGG|GAGTTTTCAT|AGCCGGGATC|CTGCAGCTCC|CGTTTCTGC|5220|
|TGCCGCCCTG|CTCTGCTGCT|GACTAGGATA|GCAGGGCTAA|GGACATGGTG|GGAGCCTGTC|5280|
|CCAAACAGCA|CTTCCCCCGG|CCTGGACATG|GTGCCAGTGC|CTTCTGTGTA|TTCGTTCACT|5340|
|GAGTCCCCAC|AACACCCTG|TGAAGCAGGC|GCTGTCATCA|CCTGATGCAT|GAGGAAGCCC|5400|
|ANCGTCATGG|GTGTGTGACC|TGCCTGAGGT|CCCCCACCTG|GTGGGCAGGG|GTGTGGCCTC|5460|
|TGCCCCATCC|TGGTGCCACG|CTGGCTTCCT|CTGGGATACA|CTCGTCTGAG|CTGGGCTCCC|5520|
|TGTGGGCAGC|CCTGTGCCCT|GGGAGGTGGA|AAGAGGGGCC|TGCGGGAANG|GAGAGGTGGG|5580|
|CAGGGGGAGG|CTGGGGCCCG|GCTGTCTCTC|AACGACTGTT|TGCTTCCCCA|GTCTTCTCAC|5640|
|CAGGCCAGTG|GGAGCCAGCC|CCTCCCACAG|TTGGCCAGTG|GGCAGCCTGG|GGCCTCTCTC|5700|
|TTCTTCGCTC|TCCTTCCTCC|TCTCCCCTCA|CTTCTCTATC|TCTTCTCTCT|CCACACAGCG|5760|
|TTTCTGGACC|GCCTGCCTCA|GTGTCCCTCT|CGGGGGTGGC|CTGGGGTCTN|GGTGTCTATG|5820|
|TTGGGGGGCT|GGGAAGGCAN|TNACTCTTCA|TTTGCTGCGT|CCTGCTCANT|GGCCTGGGTG|5880|
|GGATGTGGCT|GAGGTGTGAC|TAACCGTGGC|TTTGTCTCTG|TCTGTCTCCC|CCAAACCCCG|5940|

-continued

```
TGCTCTGCTG TGCCTTCCCG CGCGGCCCCT CACCCGCCGC CGACCCACAG CTCCGGAAAG    6000
GCCCACCAGT CCCTCCGCCT CCCAAACACA CCCCGTCCAA GGAAGTCAAG CAGGAGCAGA    6060
TCCTCAGCCT GTTGAGGAC ACGTTTGTCC CTGAGATCAG CGTGACCACC CCCTCCCAGG     6120
TCAGCCGCGG CCGCCGCGGC CCAGCTCTCC TCTCTTCCTG CCCTCTCAGG GCGTGCATGG    6180
CCTTCATCCT CTATGCTTCT GTCTCAAGAG CCAGGAATCT GGCCAGAGAG AGTGTCAGTT    6240
TCCCTCTCTC ACCCTTTGTT CCCTCCATCC ATCATCCTCC ATCATCCTCC ATCACCCATC    6300
TCTGAGCATG TACTAAGGCC AGATGCAGGG CCGCAGAGGG GAAGGTGCCG CCTCTCCCGG    6360
CGCAGCAGTT ACATCAGCAG CGCCCTCGCG ATGCAGTGGG TGCTATGGCA GAGGGGATCG    6420
GGGAGTGTGG AGGACTGTGG CTGTCAGGGA AGGCTTCCAG GGCCAGGGAG AGTTGGAAGG    6480
TCCTGGAATG GCTGAAGCAC CTGGACTTCA GCTCCACAG CTGCTGTCAG CCCCTCGAGG     6540
GCGGGGCAG CGGCCAGGCT GCAGGGCANA ACTGCCGGTG TGCAACACTC CCTAAGAGGC     6600
GTGGAATGCC CAGATACAGC AGGGAGCCAC CCAGGGGGC TTGGGTCTCT CCCGACGGGC     6660
CCTTGGCTCA GCAAGGAGCC ACGCAGAGGG TCTTGGGTCT CTCCCAGTGG GCTCTTGGCT    6720
CAGCCGTGGA GGTGCCTCTG GGAGCCCGG CCCACAGCCC CAGGTCTTAC GTCCTTCATG     6780
GTGGAGGTCG GGCTGGAGTA CCTGTGCTGG AAGCGCATCT TGCCAGTGCT GGAGTGGGCT    6840
GACGTGTTGT CAGATTTGCC CAGAGGTGGC CGGCCTTCCC CGCACTCCCC GAGAGCTGAC    6900
TGCCTCCTCA AGGTCCAGCC CTCAAGGCCT CACCTTCCTC CTGTGGGTTA GCCAAGAACC    6960
TTCCCACACA AACCTCCCCT GTTAGGAAAG CTGTCCATCC AAGCTTGTGG TGGCCTCCCA    7020
ACAAACACCT TCCACACACT CAAAAACCCT ANTGGGGANT AGTTTGGAAG GTTTTAATTT    7080
TNGGGAATTT GCCCNCTGGG AACTTGCAAA CANTGGTCCC CTGCTAAGAA AGGTTTGGGA    7140
NTGGTGGGCC TCCAACCCCC TNTGCNAAAA NNTAGGAAAT TAAAACTNAG GAACCNAAGG   7200
CNNCCGCCNC TTGCNTTTGT CCATGAAANN NNNNGCCCAC GGGCTTACCC GGNTGTGGGG   7260
TGGTGNGTAG CGTGTGTCCN TGACATGGAG GGACNGTCCC GGGCCTGCAT GGCGGGGTGC   7320
CACCTGCCGG GGCAGCACAG CGAAGGGATG GTCAGCTTTT TGGCGGATGA CCCTCCCCTC   7380
AGCACATGAC GGATATTGCT GCGTGGGTTG GCTGACTTTT ATGAGACAGG AGGGAGGGGT   7440
GTTGCTGGGG CAGGGTGGGG GCCACTGGGG AGAGATGCTG GCCGCCCGCT GGTGGGAGGC   7500
ACCTCGAGGC TGTGCACCGG CGTCCTCAGG GCTCCTTCAG AGACGGCCGG TTATGGGGCA   7560
GAGCAGTGAC CTCCCGACCC TGGGTTCCCC AGACAGGGCT GGACCTAAAG GAAAGTCAGC   7620
TGCTGGGATT GGCCCAGGGC AGGGCTTGGG GCCTAGGGCC CCTGGTTCTA GGAAGTGAGT   7680
CCACTTGGCC TGAGCTGTCT GACACCTTGG CTTGGCCATG TGGANTGCTC CACGCTTGTC   7740
CCCTGAGTGC AGGACAGCTG GTCTTCTTAG GACTGAGGAC CTTGGTNTCT CCCAATGGGC   7800
CTTCGGTTCA GNTATGGAGT GCTTNTGGGG AGCCCGGCCC ACAGCCCAG GTCTCACATC    7860
CTTCATGGTG GAGGCCGGGT GGGAGGGCGC CCCTGTCAGT GTCCGGTGCC TGTCAAGAGT   7920
GTGTAGAGCC GGGAAGCCGC TGGCCTGGGC TGCGGGGCTG GAGTTCTTCC AGCACTGCCT   7980
GAGGGCCCCG GAGGGGAGCA CCCCGGCCAC GTCCCTCTCC TTTTAAACCT GGGCAAAGTT   8040
CTCTCTGGCC CCCAAAGGGA AGCCCCAGGT ACAAGATGGA GACCGCAGCC GAGCCAGTCC   8100
CTGCTCCTCA GAAGGCAGCT TGTGCCCTGG GCATGGATGC TGCCCAGGG CTCACCGGAG    8160
TCATTGTCCC CGCCTGTGCC GGGGGCTCTA AGGAAGCCCC TTCCTCCCAT GCTAGTCTGG   8220
CCCAGCTTAT GGGGAGGCTT GTCCCTGTGT GGCCAGGGCC ACCGTGTCCC ATCCCTGGGG   8280
CCATGCCTGT CACATGCCTA TTCCTGGGCT CACTGGAAGG AGATCTTGGC GAGGGCTGC    8340
```

| | | | | | |
|---|---|---|---|---|---|
| TGGGAGGGGT | CAGGGGCCTG | CAGTTTTAAC | CCAAGTGCCC | CGGGTGGTTC | TGAAGCCCCC | 8400 |
| GAATGTTGAA | GACCCCACTT | TGAAGCTTGG | CTGTTGGGCT | TTGTGGCTGG | CTCCACTCTT | 8460 |
| TCTCCGTCCC | TGGAGCTGAC | GGCTGGTGGT | GTCGCCAGAG | AGTGACCTGC | CTGTCTGGGG | 8520 |
| TGGAGGAAAA | GCCAGTGTGA | AGTCTCTGCC | TTTGGAACTT | TCCCAGTCGG | GAGCACTGAG | 8580 |
| GGTGGCTGTG | GCATGGTGTT | ACTCTCGCCA | CTGGGGGGTA | GCAAGATCAG | CAGAACTCTT | 8640 |
| GGCGCAGGGA | GCGGAGAGGA | GGTTCGGGCA | TTGGTAGGGA | GGGGCCCACC | AGTCTGTGGA | 8700 |
| TGGTGGCGGA | AGAGAGCTGG | GGCCTGGTGC | TGGCCCTGCG | GGGTGGCGGC | CACGGGCGGA | 8760 |
| CCTATGACTG | GGAGTTTGAG | GCGGGCACTG | GGGTCGTCCT | CCTGGTGTGG | GCGGGAGCCT | 8820 |
| GTGCCGGGGC | GCGTGGCTTT | GGGCAGTGCT | CCCGTGTGTG | AGGTGGATGA | GTTGGTGCCT | 8880 |
| GGGCTGTGTG | CCAGCGTGTG | TGCGTGTATG | TGCGCTTGCT | CTGTGCATGC | GTGGTGTGTG | 8940 |
| TATGTGTGTG | TGTCCACGCG | TGTGCCTGTG | CCTGCAGTGT | CTGCCTGGGG | TGAGGGCTCC | 9000 |
| CAGCTTAACA | CTAACTGCTT | CCTCCTCTGC | TGCTGCTGCT | GCTGCCAAGT | TTGAGGCCCC | 9060 |
| GGGGCTTATC | TCGGAGCAGG | CCAGTCTGCT | GGACCTGGAC | TTTGACCCCC | TCCCGCCCGT | 9120 |
| GACGAGCCCT | GTGAAGGCAC | CCACGCCCTC | TGGTCAGGTT | GGTTGTGCCC | ACCACTGCCC | 9180 |
| ATGGGCCCAC | CAGCTTCCAG | GTGCCCAACC | CTGGGCTCAT | GTTGCCTATT | GGCCACGTGA | 9240 |
| CCCCAGCTAG | GCCTGGGTCA | CTGCCCTTCC | CCTGGCACCT | CAGCCTTCAG | CCCTCATCAC | 9300 |
| CTCCTGGTTG | TAGGGCAGGA | AGCAGCCCCT | GATCAGCTGG | GAGAACTCTC | AGTAGGGGGT | 9360 |
| TACTGAACAC | TTCCTGGCAA | CTTTGTGCTC | ATCGCTTGGG | GCAGAAGCAT | CCTGGCTTGG | 9420 |
| GGTCTTGAAG | CTCCCTGAGA | GGTGTCGGGA | GCTCGGCCAC | CTGCAAATCT | TGGAGTCTAC | 9480 |
| CTGGCTCCGA | GCCACTCCTG | TGCCTGCTGG | GCTGGATGGC | CTGGGGCGAG | CGGGGGTAGG | 9540 |
| GTCCCTGGG | GACTGCTTGC | CGCCCTGTCT | CTAACCTCTG | TGCTAACTGT | CCTTCTCGCC | 9600 |
| CTCACTGCTG | CGCTCAGTCA | ATTCCATGGG | ACCTCTGGGA | GGTTAAGCTG | CACTCTGCTC | 9660 |
| TTTGTCCACC | CCCTGGGGGA | ACCACTCTTT | CCCGTATGTG | TCCAGGCCCA | CATGATCATA | 9720 |
| GCCTGTTCAC | AGGTGCATGC | ACCCCACACA | CCCCCCACAA | GCAGGACACA | CAGGCACGTG | 9780 |
| CTCACGCACA | GGGAGNTGGT | GAAGCCACCC | GCCTCCAGCC | ATTNTGNTGC | TTCTCCCTCT | 9840 |
| GGCAGGCCCT | TGGAAAAGGG | GATCTTCGGT | TTAGCTTGAG | ACAGGGGTCC | CCTGAGATCT | 9900 |
| GGTCCTGTTT | TCACAGCCTG | TGAGTGTTTG | CCTCCAGACA | GAAATGGGCC | GGTCACCCAG | 9960 |
| GATGGACGAG | TGTCCTCAGG | GTGTGGGGCA | GGAGGGCCTC | AGGGTAGAAG | GTTCTTGCCT | 10020 |
| TCTCTGAGCT | TTTTGGCAGT | GGGGAGCTGT | TTGCGAGGAA | GGGGAGAGGG | GAGGAATGGA | 10080 |
| TGGTTTGAGA | GAATCAGGGA | AGACAGGGTG | TGGCTGAGTG | CCTTCTGAGA | GCAGGGCCTG | 10140 |
| CAGGCAGGTG | CGAGGCCATC | TCACACAGCA | CCATGTCACT | GTCACCTGAT | AGCTCAGGAC | 10200 |
| ACAGAGGCTC | AGGGAAGGCT | CAGTACTTGC | CCAAGAACTG | GTCATGGTAG | AGCCAGAATT | 10260 |
| CCAACAGGGT | CTCCTGGGCT | CTGTCCCTGA | GACCCCTGA | TACAGGCAGA | GATGCTGGGA | 10320 |
| GGGGCAGGCG | GGTGTGCAGG | CGCCCTTGGG | GCATGCGCTG | GCAGCCCAGG | CTCCTGGGAG | 10380 |
| CTCTGGAGGC | TCCACCGCAG | GATTTCCCTC | TGGAGGAAGC | CAGAAAGAGC | CAGCCTGGTG | 10440 |
| CGAGCTGGTA | GGGCCATTTT | GACAAGTGGA | TTTCGGTAGG | TGCTGAGCTT | GGGCAGCACA | 10500 |
| GTCACACCTG | CCTGTCCCTT | TGACAGTGGT | AGGAGAGAGG | ATGTGGGAGG | CGGGTGGCTG | 10560 |
| GCCGGGCTCC | GCTGGTACCC | ACCCTGCCCC | CACCAACCCC | AGCCGCTGGT | GACATTTTCT | 10620 |
| CTTGTCTTGT | GATCCTGCCC | ATTGCCTTTC | CACCCCGGCC | TCCCCGCCCC | CTCCCTGTTC | 10680 |
| TCTCCTCGTG | GCCTGTTACC | AGCCCACAGA | GAGTCCAGCC | GGCAGCCTGC | CTTCCGGGGA | 10740 |

```
GCCCAGCGCT GCCGAGGGCA CCTTTGCTGT GTCCTGGCCC AGCCAGACGG CCGAGCCGGG   10800
GCCTGCCCAA GTAAGTGCCC ACCTCCAGCC CCTGTCTGGC TTGTCCCCAG TCTCTAGGGG   10860
TGCAGCATGG AAGGAGAGCC CCGAGGAGGG GTTGCAGGAG GGACCAGGCC ACCATGGATG   10920
TGAGGGTGAG GACAGGGTCC TGAGCTAGGC TGCCCCAGCA CGGGCTTGTC ACCAAGGCTG   10980
CCAAGGATGA ATGAGCGCAC TGGGCGCATC AGCCCTCCT GCTTGCCCAC CCCAGCCCAA    11040
CCTCCCACGC AGGAAGACAT TTAGGAACAC CTACTGGTTT ATGCCAGCAC TTTCCANGTG   11100
TTGTGTCCCC CTGCCATGGA TTATNTATAG GTGCAGCAAG ATCTTGCCAC CTGCCGGTCA   11160
AGCAGGGTGG GCGGGCGGTG GCTGTGGTGG GCGAGGTCTT GGTGCCGAGA GAGCAGGGCC   11220
TGTGAGGCGG GGTTGGGGGT GGCACTATGG GGCTTGCACT GGGTTCTTCA CAGCATTGTC   11280
ACTCACATCC TTGGGCNTGC CAGCGCNTAC TATTCAGCTG CTTCCCCGGC CCAGGGCCCA   11340
GCTTGTCCAG CAGAGGCTCC CNTGGATTNT TCGAGGCACT GGGCAGCTCT AGACCNTGCT   11400
GCCAGCCAGG CGATGCCCCC GGCCCTGTTG CTTGGGTGCT GCCCTCCTGT GGCCTGTTTC   11460
CTGTGTCCTG GCTGTGTCCT GTCCTGTGTC TGACCCCAAG CCGGCATTTA TGTTGCAGCC   11520
AGCAGAGGCC TCGGAGGTGG CGGGTGGGAC CCAACCTGCG GCTGGAGCCC AGGAGCCAGG   11580
GGAGACGGCG GCAAGTGAAG CAGCCTCCGT AAGACAGCAG GGACAAAGCC CTGCCTTTTC   11640
CTCCCTGCCG CCCGCCTGCC TGTCCGGGGC TCCCCTGTGG CCCCTGATGG TGCTGGTCCA   11700
GGCCTGGCTC CTGTTGAGGA AGCTGGAGGC GGGCCGGTCT GGCACCAGGC GCAGACACCT   11760
TTCTCCCCTC CCCGCCCCTC TTCTCCTCGG TGGCCCTGGC TGTCCTTGGA CCACCTTCCC   11820
TGCTCAGCTG ACCCGTACCT CTGCCACCAG AGCTCTCTTC CTGCTGTCGT GGTGGAGACC   11880
TTCCCAGCAA CTGTGAATGG CACCGTGGAG GGCGGCTGTG GGGCCGGGCG CTTGGACCTG   11940
CCCCCAGGTT TCATGTTCAA GGTGAGCCCA CAGCCTCTGA CTGCTGCAGT CCCTCGGTGC   12000
CCTGGTGGGC AGATGACAAC CCTGAGCCTC AGGAGACTCT GTGGTTTGCC CAAAGTTGTG   12060
CAGGCGCTAC TAGGTCACTC CCAGCCAGCA AGGTGGCATC TGANCCCCAT ACAGTCCTGC   12120
TGCTTTTGAG CACTCCTGGT CTCCATACTG CCACCTGCAC CTCCCACACG CAAGGCCCGT   12180
GCTCTGTGCA GGGCTGGAGG TGGGACGGAA GGTCTGACTT GCGATCCGCA TCCTCTGCAG   12240
GTACAGGCCC ACCACGACTA CACGGCCACT GACACAGACG AGCTGCAGCT CAAGGCTGGT   12300
GATGTGGTGC TGGTGATCCC CTTCCACAAC CCTGAAGAGC AGGTGAGGGC TGGGTGGGGC   12360
CCCCACACCN CANGGGGACC ACCNNGCATC CTGGCTGCGG CTGGCACCNC CGTNGCGGAT   12420
ACNCGCCATT CAGGGGGCAG CAGAGGCCCG CGAGCACCAG GGCTCCCGCG CCAACTGCTC   12480
CTCCCCGCCC TCCACGTCGG GCTTTTTCCT CTCTCCCTCT CCTCTCCCTT CCCTTGGCCC   12540
CTCTCCTGTT AGGCCTCTCT CTCTCCCTGT CCCCATACCC GCTTCTTCCT GTAGCCTCTG   12600
CTTTCTTCTC CCCACGTCCC CCCTTTGCTC AGGCGCTCTC AGCTCTGCCT CTGTCTCTCC   12660
CCTTCTCCTC TCCTGGCAGC TGTGCCTGAG GCCTGCCTCC CTCCTGGGAC AGGATGCTTG   12720
ACCCCTCCTG CCCCGCCCAC AAGGTGCCCA CCCTGCAGCC AGCCGGAGCA CTGGTTGGGC   12780
TCATGAAGCC CCGTGTGCCG TCCTCGAGG CGGGCCCTGC CCTGTGCACN CAGGGCCATG    12840
GGCTTCCCAG CTGTGTCCCC GGCTGAGGCT CACCCACGAT GCCTTCCAGA CCCTTCTCCT   12900
CCTGCTGTGG CTTCATGTTA ATCTCCTGGA AGTGAGGGCT CCTGTTGAGC CTGGGTGGGT   12960
GCTAAGTGTG TCCCTCCTAA GTCTTGGGAC CTCCTGGATC TGGGTCAGTT TGCCCCTCCC   13020
CAGGGGGCCT TGGAATNATN GGCAAGGAGC TTCCCCGNTG TGTAGAACCN AGCTTTGNTT   13080
GTGGGGGGTC GGTGGTGCCA TGTGGGCATC TGGTTCTTCC ACGGTTCAGC CCCTGAGCAC   13140
```

-continued

```
NTCGGGCTGT GCACAGAGGG CCTGGCCGGT TATTCCTGCT TCCAGAGAAC ATGTTTAGCC      13200
ATCAACGCTT CTGTGTGAAT AGGTTATCAG AGCGGCTGAG GGTGACAGTG GGTCTGCCTG      13260
GGTCTTGGAT GAGGCCGACC NTACTGGGGG TCCTGGGCTG GGATGTAGGG GTACCAAGTA      13320
CTTACTGAGG TCCGGGGCAG GAGGCCTGAG TGATGAGGAC CTTGTGGGCC TGGCACTGAT      13380
TTGGCCCTTT CTCNTAAGCC CCCAGGTCTT CATGGACCTC CTAGTGGGCC AGCCCTGGCT      13440
GGGTAGGATT TCAAGCAGAC TGCTACCCAG AGCCCACAGT GAGAATTGGC CTGGGGNTGC      13500
TGGAGGGGGC TCAGGGCATG AGTAGGGTCT GTGACCAGGC TGACAATGAC ACAGAGGGAA      13560
ATAACAAAGA CCCAGGTAGG CCCCAGGCAC AGCCCAGCTG CAGGGGCAGC CTCGGCCCAG      13620
CCACTGGCAG GAGTGGATGG CCATACGGCT CCCCGTGACC CACCTGGGGC CAGGGGCCTG      13680
TCAGCACTCC CAGAGAAGGC CCTGCGGGTG TCAGGATTGA AGCAAAGGGC AAGTGGAAGT      13740
TGGAGGGACT GGTGGGATGG CCCCAATCCC TCTAGAATTG TAACTTGTTG TCACTCCCAA      13800
AACTTCGTGG GGTTGTTTGA NAAGCCTGNA ATCCTGGAAG GGCTGATGTG CACATCATGC      13860
ATGCAGTGGG ACTCATCAAA ACCAGCACG AATGGTTAGA TCCACCTGCG GACTCACAGG       13920
CTGGCTCCTG TGGTGCCTCT GGGCAGGAGC CTCAGCCAGC ANCATCAGGG AGTGCTGCCT      13980
GGAGGAGGTG TTCTCAAGGT GGGCTTGGCA GGCTGAGGCA CCAACAGCAG GAGGAGGGC       14040
CGTCTTCCCA GCAGGTTGGA GTGGGATGCG TGCCCTGTGG GGTGGANCCC CTTGCTCATC      14100
CCTGTGCGAC CTGNTGCTCT GCCCCTCAGG ATGAAGGCTG GCTCATGGGC GTGAAGGAGA      14160
GCGACTGGAA CCAGCACAAG AAGCTGGAGA AGTGCCGTGG CGTCTTCCCC GAGAACTTCA      14220
CTGAGAGGGT CCCATGACGG CGGGGCCCAG GCAGCCTCCG GGCGTGTGAA GAACACCTCC      14280
TCCCGAAAAA TGTGTGGTTC TTTTTTTTGT TTGTTTTCG TTTTTCATCT TTTGAAGAGC       14340
AAAGGGAAAT CAAGAGGAGA CCCCCAGGCA GAGGGGCGTT CTCCCAAAGT TTAGGTCGTT      14400
TTCCAAAGAG CCGCGTCCCG GCAAGTCCGG CGGAATTCAC CAGTGTTCCT GAAGCTGCTG      14460
TGTCCTCTAG TTGAGTTTCT GGCGCCCCTG CCTGTGCCCG CATGTGTGCC TGGCCGCAGG      14520
GCGGGGCTGG GGGCTGCCGA GCCACCATAC TTAACTGAAG CTTCGGCCGC ACCACCCGGG      14580
GAAGGGTCCT CTTTTCCTGG CAGCTGCTGT GGGTGGGGCC CAGACACCAG CCTAGCCTGC      14640
TCTGCCCCGC AGACGGTCTG TGTGCTGTTT GAAATAAAT CTTAGTGTTC AAAACAAAAT       14700
GAAACAAAAA AAAAATGATA AAAACTCTCA GAAACGTGT GTGTATTTGT TCTCCCTCTT       14760
CTTGTCCGTG AGTGCGGATG GAACCGTGTN ATCTGTGGCT TTCTTACTGA GATGGTCTGC      14820
CCCCGAAGGC CCGCTGCCCT GNCGCTGGTG CACCACAGGG CTTCACCCCC TGTCCCCTGG      14880
GGTTCTTAGG GGTGGTCACC TGGANGTCAN GGACTGGGGG CTTGGGTTAA GGGGCTTGGC      14940
CACCCATCTC TTGTCCCANA AATCTTGCTN ACTGCCCCCC TAACT                     14985
```

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:7:

```
Phe Thr Arg His Pro Pro Val Leu Thr Pro Pro Asp Gln Glu Val Ile
 1               5                  10                  15
```